United States Patent [19]
Lesnick

[11] Patent Number: 4,592,360
[45] Date of Patent: Jun. 3, 1986

[54] IMPLANTABLE EXTERNALLY PROGRAMMABLE MICROPROCESSOR-CONTROLLED TISSUE STIMULATOR

[75] Inventor: Alan F. Lesnick, Miami, Fla.

[73] Assignee: Cordis Corporation, Miami, Fla.

[21] Appl. No.: 451,598

[22] Filed: Dec. 20, 1982

Related U.S. Application Data

[62] Division of Ser. No. 195,665, Oct. 9, 1980, Pat. No. 4,424,812.

[51] Int. Cl.$^4$ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,019,518 | 4/1977 | Maurer et al. | 128/419 R |
| 4,163,451 | 8/1979 | Lesnick et al. | 128/419 PG |
| 4,164,945 | 8/1979 | Hartlaub | 128/419 PG |
| 4,222,385 | 9/1980 | Backhouse | 128/419 PG |
| 4,404,972 | 9/1983 | Gordon et al. | 128/419 PG |

FOREIGN PATENT DOCUMENTS

| | | | |
|---|---|---|---|
| 0004243 | 9/1979 | European Pat. Off. | 128/419 PG |
| 2738871 | 8/1977 | Fed. Rep. of Germany | 128/419 PG |
| 1082752 | 9/1967 | United Kingdom | 128/419 P |
| 2002156 | 2/1979 | United Kingdom | |

Primary Examiner—William E. Kamm
Attorney, Agent, or Firm—Henry W. Collins; George H. Gerstman

[57] ABSTRACT

A microprocessor-controlled implantable programmable stimulator includes a pulse generator external to the microprocessor for producing stimulation output pulses to multiple electrodes. A single chip microprocessor accompanied by a ROM implements a stored program data processing system which sets various latches to establish the desired pulse parameters. Externally transmitted parameter data is decoded by the processing system, confirmed by two-way telemetry and loaded into control registers. The microprocessor obtains corresponding stored values from parameter tables in the ROM, and then sets the amplitude, rate and width latches. The pulse rate and width latches preset discrete rate and width down counters operated by respective slow and fast clocks. To conserve power, the fast clock is enabled only briefly each time the rate counter times out when it is time to issue an output pulse. When running, the fast clock replaces the slow clock input to the microprocessor. The timed-out signal from the rate counter generates an interrupt request to the microprocessor which calls a subroutine to reprogram electrode polarity before enabling each output pulse. This system allows several electrodes to be alternately connected as anodes and cathodes. An internal machine cycle counting routine disables the interrupt capability during the off portion of a scheduled on/off cycle and programs the rate to a fixed minimum. The continuous slow clock can be turned off by a reed switch whenever the rate counter is not in the timed-out condition. Reception of the first externally generated data pulse turns on the fast clock.

8 Claims, 12 Drawing Figures

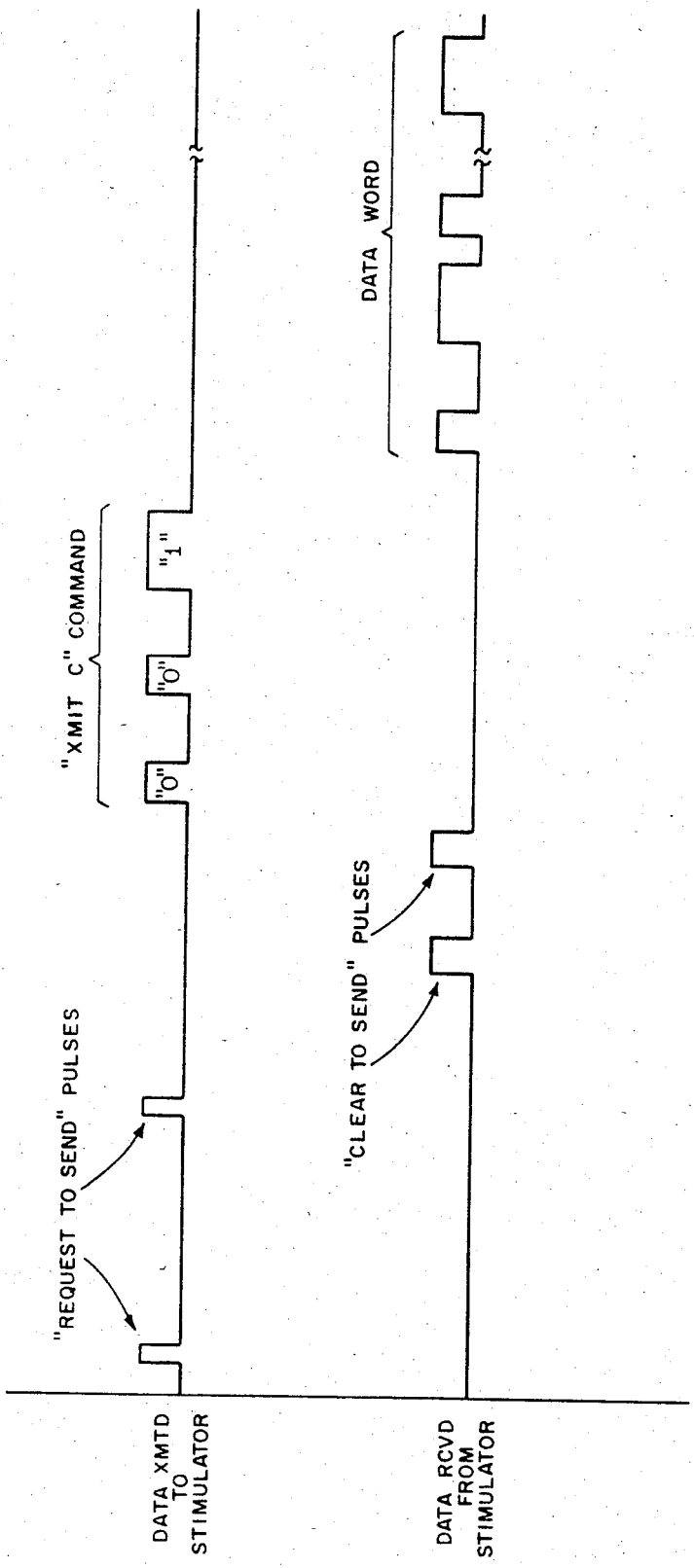

```
M
0000 7100 F801 B1B3 BFF8 E1A1 F8BB A3F8 A1AF;
0010 F800 B5F8 1CA5 F8F0 B6F8 A0A6 30D3 E070;
0020 0034 2B1C 9C3A 2171 4030 7671 40C4 C4C4;
0030 C4C4 C4C4 C47B F806 C4C4 C47A FF01 3A3C;
0040 7B7B C4C4 C47A D3D3 D33C 793C 793C 793C;
0050 79FB 0432 ADFB 04FB 0532 D3FB 05FB 0232;
0060 97FB 02FB 0132 A2FB 01FB 06C2 01EF FB06;
0070 FB07 3210 3079 983A 899D BC8D AC97 A4E4;
0080 69F8 01B8 C4C4 C430 1EF8 FFA4 699E BC8E;
0090 ACF8 00B8 E030 2195 DF85 DF96 DF86 DFC0;
00A0 0147 92DF 82DF 9BDF 8BDF C001 47D3 D3D3;
00B0 D3D3 D3D3 D3B5 D3D3 D3D3 D3D3 D3D3 A5D3;
00C0 D3D3 D3D3 D3D3 D3B6 D3D3 D3FA 07F9 A0A6;
00D0 C001 47F8 03B4 95FA 0FFC E8A4 04A4 E46B;
00E0 95B2 96BB 85A2 86AB 92F6 F6F6 F6FC D8A4;
00F0 04A4 B769 8BFA 07FC F8A4 87FA CFF1 A788;
0100 FACF F1A8 04A4 6A9B A9AA 82FA 0232 20F8;
0110 04A4 89FB FFAA 8AF6 C7F9 80AA 2484 3A16;
0120 82F6 3333 87FA BFF9 80A7 88FA BFF9 80A8;
0130 C001 4787 FA3F A782 FA02 C201 4388 F9C0;
0140 A830 4788 FA3F A882 FAE0 329B 82F6 F6FA;
0150 0732 8FFC D0A4 F803 B404 BEF8 65AE 82F6;
0160 F6F6 F6F6 A4F8 03BC 92F6 F6F6 FA1E FCB1;
0170 ACEC 72BD F0AD 2484 3284 8DF4 AD9D 2C74;
0180 BD1C 3076 8DFD FFAD 9D7D FFBD C000 7997;
0190 A4E4 69E0 7000 3C96 C000 2BE0 61FF 3096;
01A0 D0B4 F808 A47B 94FE C4DF 33AD 7A24 B484;
01B0 C4C4 7AC4 C4C4 32A0 30A5 D03D CB3D CB3D;
01C0 CB3D CBF8 00B0 F879 A030 BAFE C4C4 C4C4;
01D0 C43D D7FA FE30 DAF9 0114 D3D3 30BA E170;
01E0 00E7 6DE9 6C9C E170 00E8 6DEA 6C30 DE7B;
01F0 C4C4 C47A D3D3 B3F8 00A3 43DF 833A FAF8;
0200 01B3 F8BB A3C0 0079 FFFF FFFF FFFF FFFF;
0210 FFFF FFFF FFFF FFFF FFFF FFFF FFFF FFFF;
0220 FFFF FFFF FFFF FFFF FFFF FFFF FFFF FFFF;
0230 FFFF FFFF FFFF FFFF FFFF FFFF FFFF FFFF;
0240 FFFF FFFF FFFF FFFF FFFF FFFF FFFF FFFF;
0250 FFFF FFFF FFFF FFFF FFFF FFFF FFFF FFFF;
0260 FFFF FFFF FFFF FFFF FFFF FFFF FFFF FFFF;
0270 FFFF FFFF FFFF FFFF FFFF FFFF FFFF FFFF;
0280 FFFF FFFF FFFF FFFF FFFF FFFF FFFF FFFF;
0290 FFFF FFFF FFFF FFFF FFFF FFFF FFFF FFFF;
02A0 FFFF FFFF FFFF FFFF FFFF FFFF FFFF FFFF;
02B0 FFFF FFFF FFFF FFFF FFFF FFFF FFFF FFFF;
02C0 FFFF FFFF FFFF FFFF FFFF FFFF FFFF FFFF;
02D0 FFFF FFFF FFFF FFFF FFFF FFFF FFFF FFFF;
02E0 FFFF FFFF FFFF FFFF FFFF FFFF FFFF FFFF;
02F0 FFFF FFFF FFFF FFFF FFFF FFFF FFFF FFFF;
0300 FFFF FFFF FFFF FFFF FFFF FFFF FFFF FFFF;
0310 FFFF FFFF FFFF FFFF FFFF FFFF FFFF FFFF;
0320 FFFF FFFF FFFF FFFF FFFF FFFF FFFF FFFF;
0330 FFFF FFFF FFFF FFFF FFFF FFFF FFFF FFFF;
0340 FFFF FFFF FFFF FFFF FFFF FFFF FFFF FFFF;
0350 FFFF FFFF FFFF FFFF FFFF FFFF FFFF FFFF;
0360 FFFF FFFF FFFF FFFF FFFF FFFF FFFF FFFF;
0370 FFFF FFFF FFFF FFFF FFFF FFFF FFFF FFFF;
0380 FFFF FFFF FFFF FFFF FFFF FFFF FFFF FFFF;
0390 FFFF FFFF FFFF FFFF FFFF FFFF FFFF FFFF;
03A0 FFFF FFFF FFFF FFFF FFFF FFFF FFFF FFFF;
03B0 FF03 8A03 E004 3604 B805 8F06 6607 3D07;
03C0 CD08 EC0A 9A0C 480E CE13 0216 5F1B 6A23;
03D0 D2FC F9F5 F1EE EAE6 4A3B 3127 1D17 1311;
03E0 0E0B 09U7 0504 0302 2F3D 3735 3626 3424;
03F0 1D0D 1707 1505 3222 0409 0E13 181D 2227
```

FIG. 10

!M
```
0000 E062 FF63 FF64 00F8 06B1 F879 A1F8 08B2;
0010 F813 A2F8 06B3 F8A4 A3F8 06B4 F801 A4F8;
0020 06B5 F895 A5F8 04B6 F866 A6F8 05B7 F89E;
0030 A7F8 05B8 F83F A8F8 05B9 F801 A9F8 06BA;
0040 F855 AAF8 06BB F82A AEF8 06BC F810 AC34;
0050 4F64 01E2 79D7 2279 DC08 1C22 79D6 2279;
0060 D822 79DB 081C 081B 223B 00E0 62EE 63EE;
0070 6400 E2F8 08BF F800 AFF8 02BD F874 AD79;
0080 DD22 E20F FBE2 32A1 0FFB E332 E20F FBE4;
0090 C201 1D0F FBE1 C201 9CE0 63FF EF62 2F30;
00A0 7234 A1E0 62FF 63E2 6401 79D3 0422 7B79;
00B0 D326 227A 79D3 2622 6405 F803 BD2D 35C5;
00C0 9D3A BD30 A135 C53D C735 C964 0179 D326;
00D0 2279 D522 79D5 2279 D522 79D3 2622 6400;
00E0 3072 34E2 E064 0179 D722 79DB 081C 0818;
00F0 223B 0079 D622 79D8 2279 DB08 1408 1822;
0100 CB00 E279 D922 79D7 2279 DB08 1408 1C22;
0110 CB00 E2E0 62FF 63E3 6400 C000 72E0 62FF;
0120 63E4 E279 DD22 0FFA 10C2 0082 0FFB 15C2;
0130 0200 EF63 2F0F FE33 3D0F FC0A 5F0F FA0F;
0140 5FFF 0BC3 0262 F804 BDF8 CAAD 0F32 56FF;
0150 015F 1D1D 304C 4DBE 0DAE F808 BDF8 1FAD;
0160 DE5F EFFD 093B 6D0F F9F0 5F30 710F FC06;
0170 5F62 2FE2 F802 BDF8 74AD 79DD 220F FA10;
0180 C200 82EF 622F 0FFE 338E 0FFC 0A5F 0FFA;
0190 0F5F F808 BDF8 17AD DEC0 0072 E062 FF63;
01A0 E1E2 79DD 220F FA10 C200 82EF 632F 0FFE;
01B0 33B6 0FFC 0A5F 0FFA 0F5F FF0B C302 62F8;
01C0 04BD F8CA AD0F 32CF FF01 5F1D 1D30 C54D;
01D0 BE0D AEF8 08BD F817 ADDE 5FEF FD09 3BE6;
01E0 0FF9 F05F 30EA 0FFC 065F 622F C000 72FF;
01F0 FFFF FFFF FFFF FFFF FFFF FFFF FFFF FFFF;
0200 3400 EF62 2FE0 6401 79D3 0422 7B79 D326;
0210 227A 79D3 2622 6405 F803 BD2D 3523 9D3A;
0220 1B30 0035 233D 2535 2764 0179 D326 2279;
0230 D522 79D5 2279 D422 79D3 2622 6405 3D3E;
0240 3540 6401 79D3 2622 79D4 2279 D522 79D3;
0250 2622 C000 72F8 02B0 F862 A0F8 02BD F874;
0260 ADD0 E062 FF63 FF64 03E2 79DD 22E0 6401;
0270 C000 8271 E2F8 0852 F032 7461 22EF 693A;
0280 B7E2 F0F6 5230 78F0 F633 A2F6 339E F633;
0290 9AF6 3396 30DC F8F3 30A4 F8F2 30A4 F8F1;
02A0 30A4 F8F0 5F02 F633 BBF6 33B7 F633 B3F8;
02B0 04F4 5FF8 04F4 5FF8 04F4 5FF8 F9F7 33C4;
02C0 F816 F45F 1F69 3AC5 F8FF 5F0F 32D3 FF01;
02D0 5F30 CB69 3AC5 2FE2 12C0 0273 02F6 33EB;
02E0 F633 F0F6 33F5 F8E4 5F30 C4F8 E15F 30C4;
02F0 F8E2 5F30 C4F8 E35F 30C4 FFFF FFFF FFFF;
0300 C002 550D FAF0 F6F6 F6F6 D00D FA0F 5D0F;
0310 FEFE FEFE EDF4 5DD0 2D2D 2D0D FA07 D00F;
0320 FF08 3300 2D2D 2D0D FAF8 5D0F EDF4 5DD0;
0330 0DFA 0FD0 0DFA F05D ED0F F45D D02D 0DF6;
0340 F6F6 F6F6 D00F FF08 3300 2D0D FA1F 5D0F;
0350 FEFE FEFE FEED F45D D02D 0DFA 1CF6 F6D0;
0360 0FFF 0833 002D 0DFA E35D 0FFE FEED F45D;
0370 D02D 0DFA 02F6 D00F FF02 3300 2D0D FAFD;
0380 5D0F FEED F45D D02D 0DFA 01D0 0FFF 0233;
0390 002D 0DFA FE5D 0FED F45D D02D 2D0D FA22;
03A0 FE7E 7E7E FC0F F6F6 F6F6 D00F FB02 3200;
03B0 0FFF 0433 002D 2D0D FADD 5D0F F63B C30D;
03C0 F920 5D0F F6F6 3ECC 0DF9 025D D02D 2D0D;
03D0 FA11 FE7E 7E7E 7EFC 0FF6 F6F6 F6D0 0FFB;
03E0 0232 000F FF04 3300 2D2D 0DFA EE5D 0FF6;
03F0 3BF6 0DF9 105D 0FF6 F63B FF0D F901 5DD0;
0400 2D2D 0DFA 88FE 7EFC 0FF6 F6F6 F6D0 0FFB;
0410 0232 620F FF04 3362 2D2D 0DFA 775D 0F0F;
0420 F63B 270D F980 5D0F F6F6 3B30 0DF9 085D;
```

FIG. 11A

```
0430 D02D 2D0D FA44 FE7E 7EFC 0FF6 F6F6 F6D0;
0440 0FF8 0232 620F FF04 3362 2D2D 0DFA BB5D;
0450 0FF6 3B58 0DF9 405D 0FF6 F63B 610D F904;
0460 5DD0 C002 5571 3466 E664 0179 D304 227B;
0470 79D3 2622 7A79 D326 2264 05F8 03BD 2D35;
0480 869D 3A7E 3066 3586 3D88 358A 6401 79D3;
0490 2622 79D5 2279 D422 79D4 2279 D340 22F8;
04A0 08BE F817 AE79 D108 222E 79D1 0822 2E79;
04B0 D108 222E 0EFE FEFE FEFE 5E79 D103 220E;
04C0 F6F6 F6F6 F65E E212 3065 0303 0330 033D;
04D0 0359 0371 0387 039B 03CD 0400 0431 0318;
04E0 FFFF FFFF FFFF FFFF FFFF FFFF FFFF FFFF;
04F0 FFFF FFFF FFFF FFFF FFFF FFFF FFFF FFFF;
0500 7134 01E9 6401 79D3 0422 7B79 D326 227A;
0510 79D3 2622 6405 F803 BD2D 3521 9D3A 1930;
0520 0135 213D 2335 2564 0179 D326 2279 D522;
0530 79D4 2279 D522 79D3 2622 E212 3000 7134;
0540 3FEB 6401 79D3 0422 7B79 D326 227A 79D3;
0550 2622 6405 F803 BD2D 355F 9D3A 5730 3F35;
0560 5F3D 6135 6364 0179 D326 2279 D422 79D5;
0570 2279 D422 F808 BEF8 1BAE 79D3 2622 6405;
0580 79DA 229F 5E2E 79DA 229F 5E2E 79DA 229F;
0590 5E2E 79DA 229F FA07 5EE2 1230 3E71 349E;
05A0 E764 0179 D304 227B 79D3 2622 7A79 D326;
05B0 2264 05F8 03BD 2D35 BF9D CA05 B630 9E35;
05C0 BF3D C135 C364 0179 D326 2279 D422 79D4;
05D0 2279 D522 F808 BEF8 1FAE 79D3 2622 6405;
05E0 79DA 229F 5E2E 79DA 229F 5E2E 79DA 229F;
05F0 5E2E 79DA 229F FA07 5EE2 1230 9DFF FFFF;
0600 717B 79D3 4C22 7A79 D398 22E2 1230 0071;
0610 72BD 72AD F808 BEF8 14AE 4D5E 1E4D 5E1E;
0620 4D5E 1E4D 5EE2 1230 0F71 72BD 72AD 72BE;
0630 72AE EE4D F33A 4D60 4DF3 3A4D 604D F33A;
0640 4D60 4DF3 3A4D E212 F880 FE30 29E2 12F8;
0650 00FE 3029 71F8 08AF F800 BF3D 5B79 D372;
0660 229F FE35 69FA FE30 6DF9 0130 6DBF 2F35;
0670 6F8F 3A5B E212 3054 710E BF72 AF9F FEBF;
0680 3387 79D4 2230 8C79 D522 308C 2F8F 3A7D;
0690 E212 3078 717B 79D3 9822 7A79 D34C 22E2;
06A0 1230 9471 72AD 8D2D 8D8D 8D3A A7E2 1230;
06B0 A3FF FFFF FFFF FFFF FFFF FFFF FFFF FFFF;
06C0 FFFF FFFF FFFF FFFF FFFF FFFF FFFF FFFF;
06D0 FFFF FFFF FFFF FFFF FFFF FFFF FFFF FFFF;
06E0 FFFF FFFF FFFF FFFF FFFF FFFF FFFF FFFF;
06F0 FFFF FFFF FFFF FFFF FFFF FFFF FFFF FFFF;
0700 FFFF FFFF FFFF FFFF FFFF FFFF FFFF FFFF;
0710 FFFF FFFF FFFF FFFF FFFF FFFF FFFF FFFF;
0720 FFFF FFFF FFFF FFFF FFFF FFFF FFFF FFFF;
0730 FFFF FFFF FFFF FFFF FFFF FFFF FFFF FFFF;
0740 FFFF FFFF FFFF FFFF FFFF FFFF FFFF FFFF;
0750 FFFF FFFF FFFF FFFF FFFF FFFF FFFF FFFF;
0760 FFFF FFFF FFFF FFFF FFFF FFFF FFFF FFFF;
0770 FFFF FFFF FFFF FFFF FFFF FFFF FFFF FFFF;
0780 FFFF FFFF FFFF FFFF FFFF FFFF FFFF FFFF;
0790 FFFF FFFF FFFF FFFF FFFF FFFF FFFF FFFF;
07A0 FFFF FFFF FFFF FFFF FFFF FFFF FFFF FFFF;
07B0 FFFF FFFF FFFF FFFF FFFF FFFF FFFF FFFF;
07C0 FFFF FFFF FFFF FFFF FFFF FFFF FFFF FFFF;
07D0 FFFF FFFF FFFF FFFF FFFF FFFF FFFF FFFF;
07E0 FFFF FFFF FFFF FFFF FFFF FFFF FFFF FFFF;
07F0 FFFF FFFF FFFF FFFF FFFF FFFF FFFF FFFF
```

FIG. 11B

IMPLANTABLE EXTERNALLY PROGRAMMABLE MICROPROCESSOR-CONTROLLED TISSUE STIMULATOR

This is a division of application Ser. No. 195,665, filed Oct. 9, 1980, now U.S. Pat. No. 4,424,812.

CROSS-REFERENCE TO RELATED APPLICATION

This application incorporates by reference U.S. application Ser. No. 153,093, filed May 27, 1980, which has now matured into U.S. Pat. No. 4,361,153 by Slocum et al., entitled "Implant Telemetry System", assigned to the assignee of the present application.

BACKGROUND OF THE INVENTION

The invention relates generally to electronic implants, and more particularly to externally programmable multimode biological tissue stimulators.

Neural stimulators hold great promise for relief from the effects of various physiological disorders. For example, electrodes can be implanted at sites in the human brain for control of neurological disorders or along the spine to block intractable pain. While neural stimulators share many of the characteristics of cardiac pacers, the great variety of neural applications frustrates attempts to adapt pacer technology and to define standard parameters. Rate, width and amplitude requirements vary by factors of ten from one neural application to another. Moreover, the optium parameters for a given patient may drift widely from time to time.

The complexity of the functional requirements suggests the use of a multi-purpose programmable generalized neural stimulator. For chronic conditions, a fully implanted battery-operated stimulator with telemetry is indicated. Because the pulse rate may greatly exceed the one to two pulse per second (pps) cardiac rate, battery drain, however, is a more acute problem. Moreover, the increased complexity of the programming variables increases the chances for error. Despite the complexity of the overall system, the power consumption and number of electronic components must be kept within bounds. The exceptionally high degree of programmable adaptability and relatively high pulse rate for the ideal neural stimulator require a wholly new approach to both the internal electronics and the external programming.

SUMMARY OF THE INVENTION

Accordingly, the general purpose of the invention is to provide a higher degree of programmable flexibility in an implantable stimulator with minimum power consumption. A corrollary object of the invention is to provide a reliable technique for establishing pulse parameter values over an extendable range.

These and other objects of the invention are achieved by a microprocessor-controlled externally programmable stimulator which includes a pulse generator for producing stimulation output pulses to multiple independently connected electrodes. A single chip microprocessor accompanied by a ROM implements a stored program data processing system which sets a plurality of multibit latches to establish the desired pulse parameters. Externally transmitted parameter data is decoded by the processing system, confirmed by two-way telemetry and loaded into control registers. The microprocessor obtains corresponding stored values from parameter tables in the ROM, and then sets the amplitude, rate and width latches. The pulse rate and width latches present discrete rate and width down counters. Separate slow and fast clocks operate the rate and width counters, respectively. To conserve power, the fast clock is enabled only briefly each time the rate counter times out when it is time to issue an output pulse. When running, the fast clock replaces the slow clock input to the microprocessor. The timed-out signal, (ZERO)-bar low, from the rate counter generates an interrupt request to the microprocessor which calls a subroutine to reprogram electrode and case polarity latches before enabling each output pulse. This system allows several electrodes (including the case, if desired) to be alternately connected as anodes and cathodes.

The microprocessor times a commanded on/off cycle with an internal machine cycle counting routine which disables the interrupt capability during the off portion of the cycle and programs the rate to a fixed minimum. The on and off time tables in the ROM take into account the rate variable frequency of fast clock intervals.

The continuous slow clock can be turned off with a magnet-operated reed switch whenever the rate counter's (ZERO)-bar output is not low. Reception of the first externally generated data pulse turns on the fast clock and software causes the microprocessor to restart the slow clock while reprogramming the latches.

In the preferred embodiment pulse width modulated IR transmissions to the implant are coded in a series of thirty bits, three command bits followed by a 27-bit data word representing selected parameters. The data word is loaded into temporary registers, confirmed by reflected signal magnetic telemetry and transferred to control registers. On and off numbers from the ROM table and electrode and case connection data are loaded into corresponding registers. After the on portion of the cycle, the off number is transferred to a cycle register which is incremented to zero by software whereupon the interrupt is enabled and the on number is loaded into the cycle register and similarly incremented. All of the registers are provided by separate scratch pad registers in a single microprocessor chip in the implant. The external programmer as well is preferably implemented by a microprocessor based system which encodes, stores, transmits, receives, decodes and compares pulse parameter data, and repeatedly checks for proximity with the implant.

BRIEF DESCRIPTION OF THE DRAWINGS

FIG. 9 is a timing diagram illustrating the telemetry handshake sequence and interrogate command.

FIG. 10 is a table of digital values in hexadecimal form stored in consecutive locations in read only memory (ROM 52) of the implant of FIG. 3.

FIG. 11 is a table of digital values in hexadecimal form stored in consecutive locations in read only memory (EPROM 102) of the programmer of FIG. 8.

In addition to the above drawings, Appendices I and II filed with the original application contain annotated program listings in machine code and assembly language and a detailed flow chart for the implanted stimulator. Appendices III and IV filed with the original application contain annotated program listings in machine code and assembly language plus a functional flow chart for the presently preferred external programmer.

DESCRIPTION OF THE PREFERRED EMBODIMENT

Figure 1:
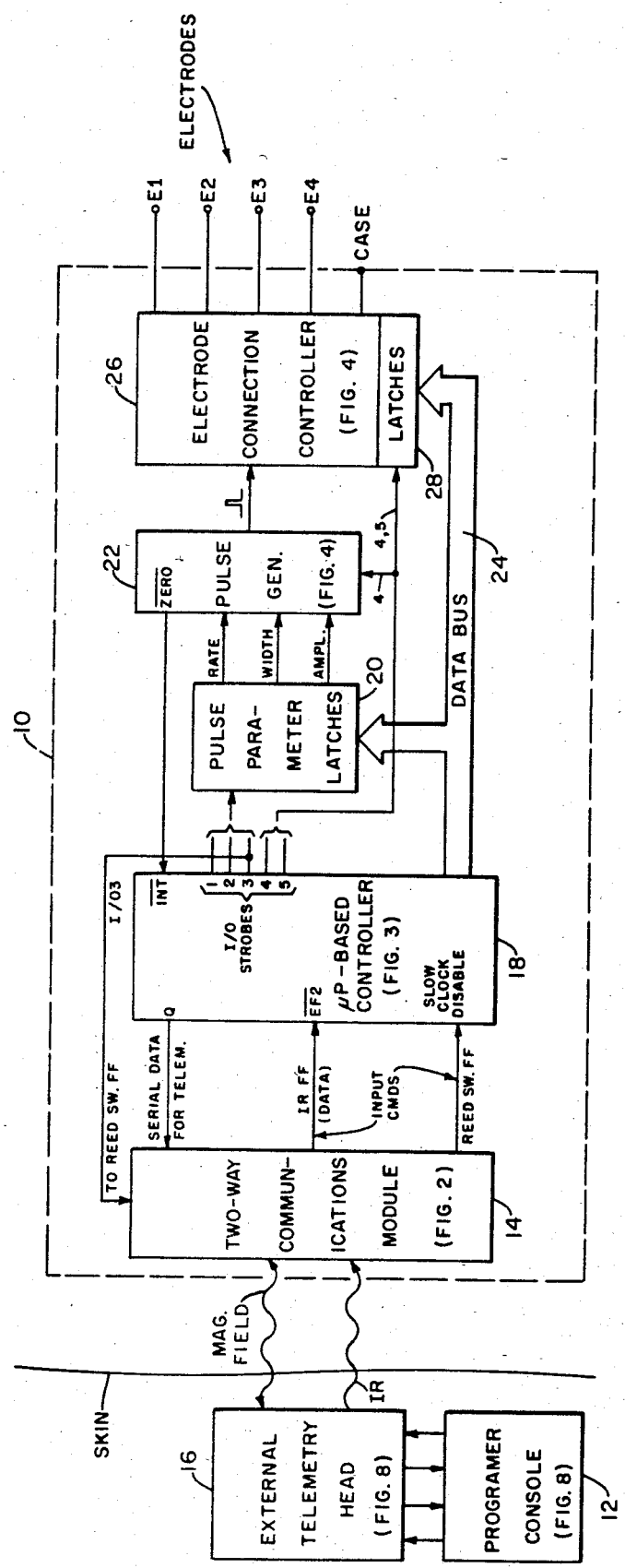
FIG. 1 is a block diagram of the programmable neural stimulator system according to the invention.

The overall system is organized as shown in FIG. 1. An electronic implant 10 communicates with a programmer console 12 via a two-way communications module 14 in the implant and an external telemetry head 16, described in greater detail in the above-referenced copending application. The communications module 14 interfaces with a microprocessor-based controller 18 which establishes and programs the following parameters in accordance with transmitted data received by the communications module 14: pulse rate, pulse width or pulse duration, current amplitude, on/off times for pulse trains, the electrical connection status of each electrode and the metallic case, (i.e., disconnected, connected as anode or connected as cathode), and whether the selected polarity is constant or alternating from pulse to pulse.

When new programming occurs, the controller 18 sets a plurality of pulse parameter latches 20 to establish the rate, width and amplitude parameters for a pulse generator 22, external to the controller 18. Individually pulse I/O strobe lines 1, 2 and 3 signal the corresponding latches to obtain the parameter values from a data bus 24, which is actually provided by the memory address bus as explained below. The output signal from the pulse generator is connected to pass current through the selected electrodes in the selected direction (polarity) by an electrode connection controller 26. The selected polarities and electrodes are determined on a pulse by pulse basis. Electrode connection latches 28 are strobed (I/04, I/05) immediately before the generation of each pulse to reacquire the applicable data from the controller 18. In addition, I/04 enables the output of pulse generator 22. By omitting the I/04 enable pulse, the controller 18 enforces an off time. The on/off cycle is timed continuously by software in the controller 18.

Figure 2:
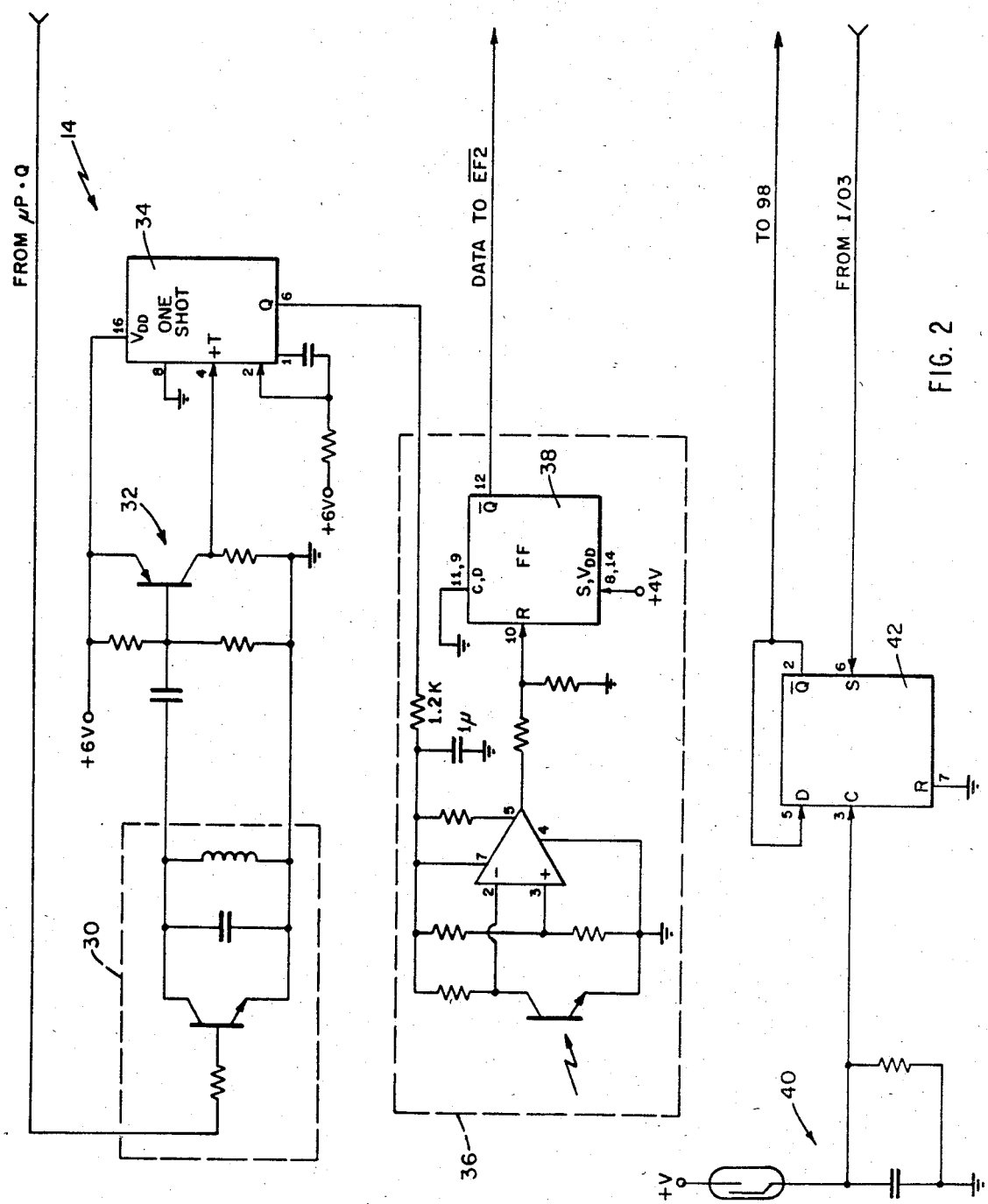
FIG. 2 is a schematic diagram of the communications module of FIG. 1.

As shown in FIG. 2, the communications module 14 includes an impedance modulated resonant transponder 30 including a tuned coil with a transistor shunt controlled by the serial output port Q of the microprocessor controller 18. The binary signal Q which gates the shunt transistor in the resonant transponder 30 changes the amplitude and phase of the signal reradiated by the tuned coil in the presence of a carrier magnetic field imposed by the external telemetry head 16. The modulation of the tuned coil load impedance is picked up in the telemetry head 16 as phase modulation, as described in detail in the above-referenced copending application.

The voltage developed across the resonant transponder coil is level-detected by transistor circuit 32 whose output actuates a monostable circuit (one-shot) 34 to turn on a normally dormant infrared receiver 36. In the receiver, the voltage drop across a phototransistor is amplified and applied to the reset input of a data flip-flop 38 whose Q-bar output forms the primary data input to the microprocessor controller, (EF2)-bar. Communication module 14 also includes a reed switch circuit 40 responsive to a magnetic field applied from outside by a hand-held magnet (not shown). The output of the reed switch circuit 40 clocks the inverting reed switch flip-flop 42 to allow the patient to turn the stimulator on and off.

Figure 3:
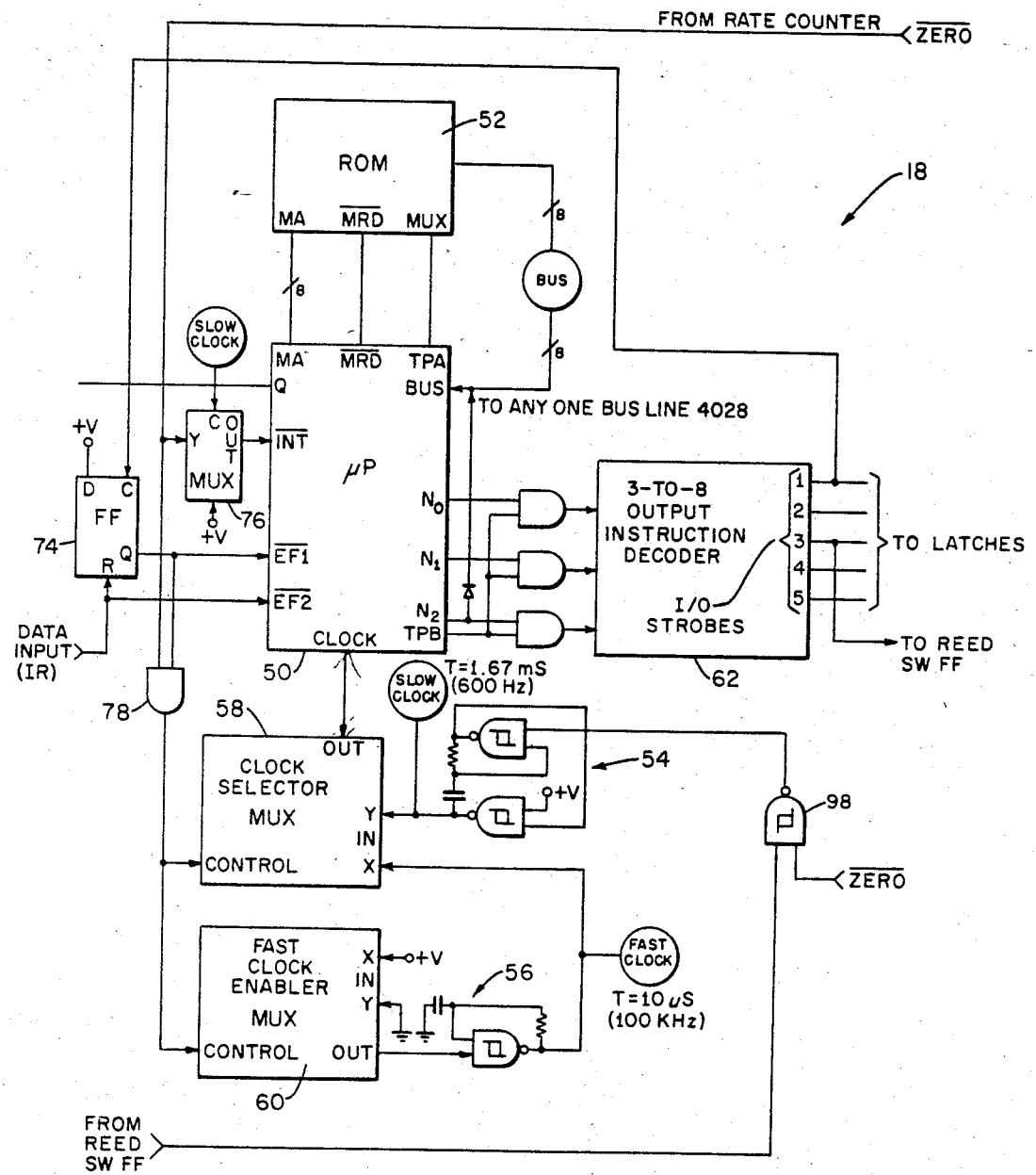
FIG. 3 is a block diagram of the microprocessor-based controller of FIG. 1.

The controller 18, as shown in FIG. 3, includes a one chip CMOS (complementary symmetry metal oxide semiconductor) 8-bit, register-oriented, byte-oriented central processing unit, in particular, the RCA CDP1802 COSMAC microprocessor 50. This particular microprocessor is characterized by the availability of 16 on-chip 16-bit scratch pad registers and 8-bit parallel organization with a bidirectional data bus and memory address (MA) bus. The microprocessor 50 is paired with a so-called 1K ROM52, in particular the RCA CDP1833, containing 1,024 bytes of fixed read only memory. The ROM contents are given in hexadecimal digit form in FIG. 10 and the second column of Appendix I. The read only memory is addressed by an 8-bit MA bus and data is transferred from the addressed byte of memory to the microprocessor on the data bus. In the preferred embodiment, the MA bus also serves as a data bus for transferring parameter data to the parameter latches.

Timing for all operations in the microprocessor 50 is provided by either a slow clock 54 (600 Hz) with a period of 1.67 milliseconds (ms) or a fast clock 56 (100 KHz) with a period of 10 microseconds. The clocks 54 and 56 are implemented by separate RC controlled, Schmitt trigger-type oscillators to conserve current. Current consumption is also minimized by using the slow clock instead of the fast clock for most operations since current drain in CMOS circuitry is proportional to the rate of operation and the fast clock operates 167 times faster than the slow clock. The clock selector multiplexer 58 applies the output of either the fast or slow clock to the clock input of the microprocessor 50. The fast clock 56 is enabled by the fast clock enabler multiplexer 60.

The microprocessor 50 is connected to receive input signals on the interrupt request line (INT)-bar, the external flag 1 line (EF1)-bar and the external flag 2 line (EF2)-bar. The (EF2)-bar input is the output of the IR receiver 36. The output of the microprocessor 50 appears on lines $N_0$, $N_1$ and $N_2$, the so-called command bits, gated by internal timing pulse B (TPB) to an output instruction decoder 62 which decodes the three bit word into five individually actuated I/0 strobe lines. The N command bits are normally low, and the 3-bit code signifies eight different output codes of which only five are used. One of the five I/0 strobe lines from the decoder 62 goes high when the corresponding 3-bit binary number is presented to the decoder.

Figure 4:
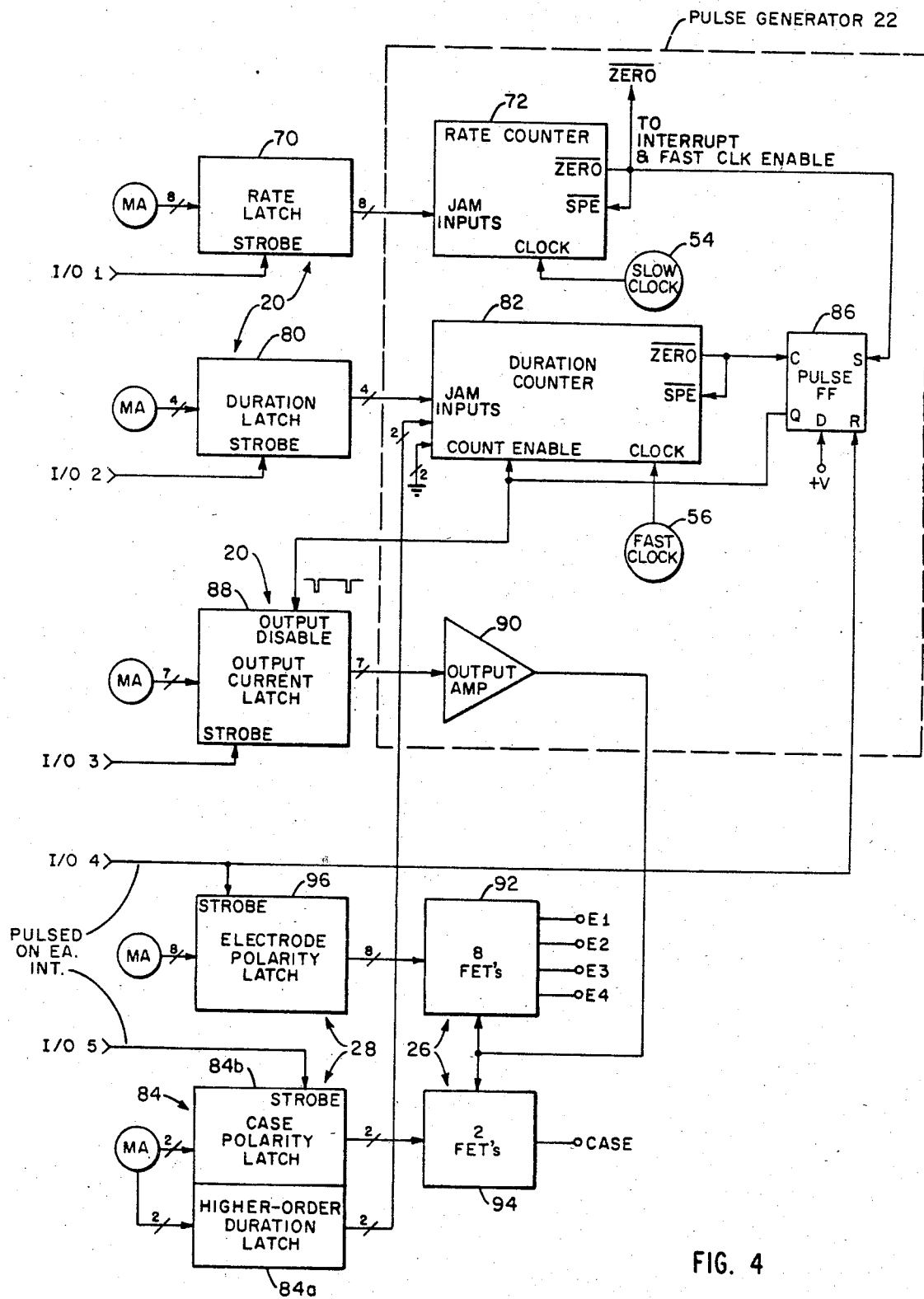
FIG. 4 is a block diagram of the pulse generator and latches of FIG. 1.

As shown in FIG. 4, the I/0 strobe lines are connected to multibit latches (groups of flip-flops). Reprogramming of the latches is achieved via the output instruction decoder 62 (FIG. 3). Strobe lines I/01–I/05 establish rate, duration, output current (amplitude), electrode polarity and case polarity, respectively via the MA bus.

When the microprocessor 50 issues an I/01 command, a binary "1" is presented to the inputs of the output instruction decoder. As a result, the I/01 output of the decoder goes high; all other outputs remain low. Since this line is tied to the strobe input of an 8-bit rate latch 70, the rate latch will accept and hold the data present on the MA bus at that time. Thus an I/01 output instruction reprograms the rate latch. Sixteen different 8-bit words, in this embodiment, designate 16 rates from 8 pps to 200 pps.

The binary number held by the latch 70 is applied to the parallel preset "jam" inputs of a presettable divide by "N+1" down counter 72 operated by the slow clock 54 (FIG. 3). The (ZERO)-bar output of the rate counter 72 is normally high. However, when a series of clock pulses equal in number to the binary number present at the jam inputs has been applied to the counter's clock input, the (ZERO)-bar output goes low. On the next clock pulse (1.67 ms later) the output returns to the high state, presetting the internal down counter back to the value of the jam inputs via the synchronous preset enable (SPE)-bar input. The effect is to divide the clock frequency by N+1 where N is the value at the jam inputs. This value is set during the programming of the rate latch and is held there by the rate latch itself. For example, a stimulator rate of 100 pulses per second (pps) corresponds to an interval of 10 ms. Since the period of the slow clock is 1.67 ms it requires the 6 clock pulses to reach 10 ms. However, since the rate counter divides by N+1, the rate latch 70 is programmed to 5 to provide the desired stimulator rate. Each time the rate counter 72 "times out", the transition low of the normally high (ZERO)-bar output indicates that it is time to issue a stimulation pulse.

In FIG. 3 the reset input of flip-flop 74 (referred to below as the EF1 flip-flop) is connected to the data output of the IR receiver 36 (FIG. 2) to alert the microprocessor 50 to incoming data. The first IR pulse causes the output of the flip-flop 74 to go low which signals the microprocessor 50 via the first external flag (EF1)-bar input, to look for data at (EF2)-bar. Flip-flop 74 is returned to its initial high state by I/01 whenever the rate latch is reprogrammed.

The (ZERO)-bar output of the rate counter 72 (FIG. 4) signals the microprocessor 50 via the interrupt request input (INT)-bar. This input is accessed through a multiplexer 76 (FIG. 3) which is used to cut the 1.67 ms pulse in half to make sure that the rate counter output does not interrupt twice on the same cycle.

The (ZERO)-bar output of rate counter 72 also enables the fast clock 56 (FIG. 3). Multiplexers 58 and 60 each apply the X input to the output on a "0" control input and the Y input to the output on a "1" control input. The control inputs to the clock multiplexers 58 and 60 are both provided by the output of an AND gate 78 which receives the Q output of the EF1 flip-flop 74 and the (ZERO)-bar output of the rate counter 72. The Q-bar output of the IR data flip-flop 38 (FIG. 2) is normally low. Thus the Q output of the EF1 flip-flop and the (ZERO)-bar output are normally high and the high output of the AND gate 78 normally causes the clock multiplexers to connect their respective Y inputs to their respective outputs. This in turn applies the slow clock 54 to the microprocessor 50 while turning off the fast clock 56. This condition is reversed when the rate counter times out and the (ZERO)-bar output goes low so that the fast clock 56 is available for timing pulse duration. The low output of the EF1 flip-flop which occurs on the first IR pulse also turns on the fast clock input to the microprocessor to enable the microprocessor to accurately decode the relatively fast pulse width modulated data from the IR receiver.

In summary, then, during each cycle when the rate counter times out, the transition to the low state of the (ZERO)-bar output generates an interrupt to microprocessor 50, turns on the fast clock 56 and steers it to the microprocessor 50. Prior to enabling the stimulator pulse, the microprocessor 50 decides whether it is in the on or off portion of the pulse train cycle (i.e., interrupt enabled or disabled, respectively) and reprograms the electrode and case connections which alternate from pulse to pulse if so programmed.

The I/02 strobe line actuates a 4 bit pulse duration latch 80 (FIG. 4) which acquires the four lower order bits of the duration code from the MA bus. There are eight possible durations from 50 to 400 microseconds. A whole byte designates each duration but the two higest order bits, b7b6, are always zero and the next two higher order bits, b5b4, are routed to a borrowed portion of a different latch, as explained below.

The output of latch 80 is connected to the jam inputs of a duration counter 82 which is implemented in the same fashion as rate counter 72 by a divide by N+1 presettable down counter. The normally high (ZERO)-bar output goes low for one clock period when a number of clock pulses equal to the preset number has been counted and reestablishes the preset count via (SPE)-bar on the next clock pulse. In other respects, however, the counter 82 differs significantly from the rate counter 72. First, not all eight jam inputs are supplied by the same duration latch 80 actuated by I/02. The two highest order bits ($b_6b_7$) are wired "0"'s and the next two higher order bits are supplied from a separate 2-bit higher order duration latch 84a which is strobed by I/05 in conjunction with case polarity latch 84b. Latches 84a and b comprise a single 4-bit latch. Secondly, the clock input is connected to the fast clock 56 which normally only comes on briefly for a 100 KHz "burst" following the low (ZERO)-bar output of the rate counter. In addition the (COUNT ENABLE)-bar input to duration counter 82 is tied to the Q output of a pulse flip-flop 86 which synthesizes the input pulse to the stimulator amplifier.

Figure 5:
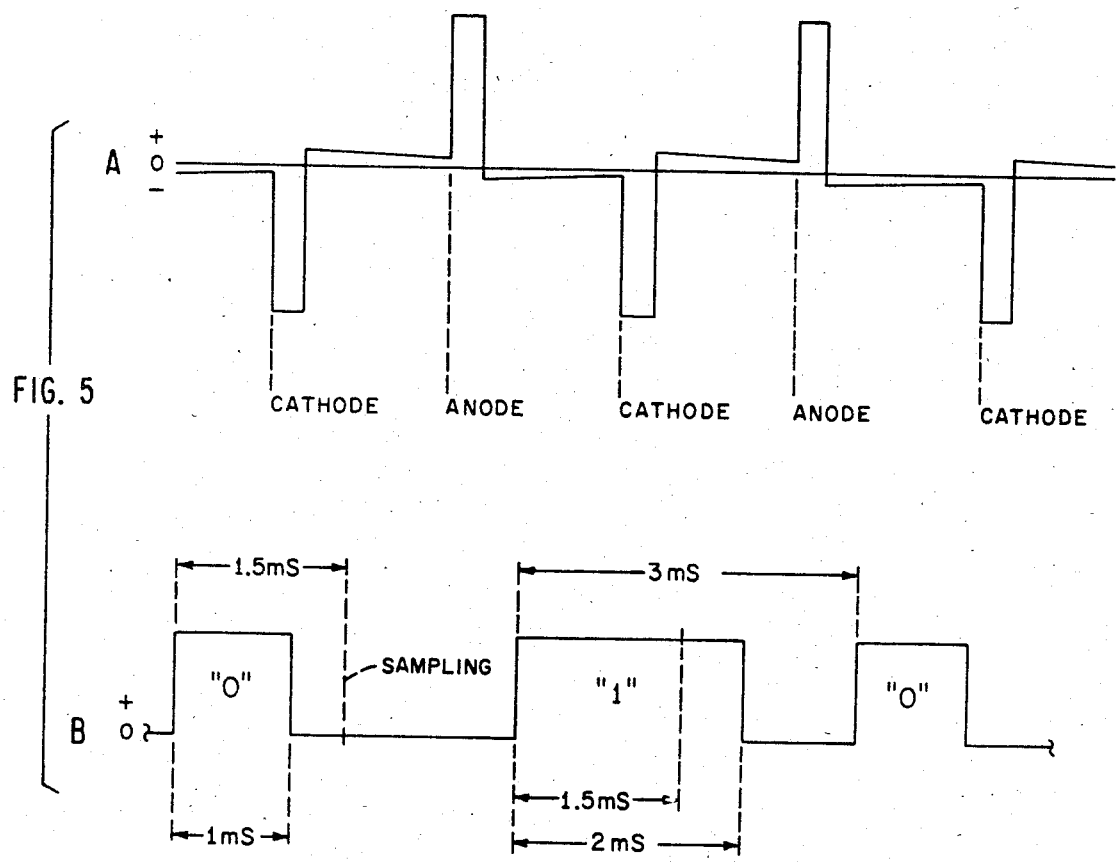
FIG. 5 is a diagram of waveforms associated with alternating polarity stimulator pulses and data transmission.

I/03 strobes a 7-bit output current latch 88 which takes the corresponding 7-bit word off the bus. When enabled by the pulse flip-flop, the latch 88 causes the selected output level to be applied by an amplifier 90 which produces the output of the pulse generator 22. The output pulse is applied to the electrodes (and the metallic case of the implant, if desired) via a bank of MOSFET's (metal oxide semiconductor field effect transistors). To allow connection of each electrode or the case as either a cathode or an anode, two FET's are employed per electrode. Thus a set of eight FET's 92 are employed for the four electrodes E1–E4 and a single pair of FET's 94 are employed for the metallic case. Each electrode can either be disconnected, connected as an anode or connected as a cathode, according to the connection pattern established by electrode polarity latch 96 which accepts and holds the 8-bit number presented on the bus when I/04 is strobed. Similarly, the case can be either disconnected or connected as an anode if continuous or if alternating, as an anode or cathode. These connections are established by the case polarity latch 84b which accepts and holds the 2-bit case polarity word on the bus when I/05 is strobed. I/04 and I/05 are strobed in that order on each interrupt of the microprocessor, i.e., whenever the rate counter 72 times out when it is time to issue a pulse unless the interrupt is disabled by the on/off cycle software. An example of the voltage waveform on a connected electrode in the alternating mode is shown in FIG. 5, line A.

The pulse flip-flop 86 is reset by the I/04 stobe produced as part of the interrupt service subroutine. This causes the Q output of the flip-flop to go low which simultaneously enables the duration counter 82 and output current latch 88, whereupon a stimulator pulse is begun by the amplifier. Timing out of the duration counter 82 clocks the pulse flip-flop 86 high since the data input is tied to the positive logic level. When the flip-flop output Q goes high the duration counter and output current latch are disabled. However, in the meaintime the duration counter 82 has already been preset by the (ZERO)-bar output to begin the next countdown. The pulse flip-flop is set in order to disable the duration counter and output current latch in any event by the (ZERO)-bar output of the rate counter 72 returning to the high state.

A stimulator pulse can only be enabled by the appearance of an I/04 strobe since this is the only input which can cause the Q output of the pulse flip-flop 86 to go low. If the microprocessor determines that the stimulator is in the off portion of an on/off pulse train cycle, the I/04 signal following an interrupt is omitted until such time as the microprocessor decides that the off portion of the cycle has ended. In the meantime, however, the rate counter 72 continues to operate and thus continues to provide interrupts and fast clock enable singals at regular intervals. The duration counter 82, however, holds at the threshold of its preset count during the off period even though the fast clock is enabled.

In FIG. 2 the reed switch 40 in the communications module 14 allows the patient to turn the implanted stimulator off and back on by disabling and re-enabling the slow clock 54 via and NAND gate 98 (FIG. 3). The slow clock 54 is on when the Q-bar output of reed switch flip-flop 42 (FIG. 2) to gate 98 is low. The patient turns off the clock 54 by momentarily closing the reed switch 40 with a magnet which inverts the state of the flip-flop 42. The Q-bar output to NAND gate 98 goes high and causes the slow clock 54 to stop immediately unless the rate counter 72 at that moment is in that one clock cycle when the (ZERO)-bar output is low and the fast clock is on. In the latter case, the clock stops when the rate counter 72 resumes its countdown and the (ZERO)-bar output returns to its normally high condition.

If programming is attempted when the slow clock has been disabled in this manner, the first IR pulse sets EF1 and turns on the fast clock. Software actuates I/03 while programming, which sets the reed switch flip-flop 42 causing its Q-bar output to go low to enable the slow clock 54.

The dual purpose of the microprocessor controller 18, when not processing a data transmission, is (1) to decide whether to omit the next pulse because the stimulator is in the off portion of the on/off cycle in a pulse train mode of operation and (2), if in the on portion, to reprogram the electrode and case connections just prior to the next pulse. The timing of the on/off cycle and the alternation of the electrode and case connections in the interrupt mode are carried out in accordance with routines stored on ROM 52 (Appendix I). In the preferred embodiment an additional function of the microprocessor is to slow down the pulse rate during the off portion of an on/off cycle so that the interval between the fast clock bursts is as long as possible to conserve current.

In the Table below, specifications for sixteen standard integrated circuit components of the implant of FIGS. 2-4 are offered only by way of illustration of one presently preferred embodiment of the invention.

TABLE

| | |
|---|---|
| Op. Amp. (IR receiver 36) | Motorola LM 3078 |
| One-shot 34 | ½ RCA CD 4098 (Dual Monostable) |
| Flip-flops 38, 42, 74, 86 | 2 RCA CD 4013 (Dual "D") |
| Microprocessor 50 | RCA CDP 1802 |
| ROM 52 | RCA CDP 1833 |
| MUX 58, 60, 76 | RCA CD 4053 (Triple 2-bit) |
| Latches 70, 80, 88, 84, 96 | 4 RCA CD 4508 (Dual 4-bit) |
| Counters 72, 82 | 2 RCA CD 40103 |
| Decoder 62 | RCA CD 4028 |
| AND Gate 78, gates for decoder 62 | RCA CD 4081 (Quad 2-in) |
| NAND Gate 98, gates in clocks 54, 56 | RCA CD 4093 (Quad 2-in) |

The two-way implant telemetry system features synchronous communication with identical pulse width modulation codes. As shown in FIG. 5, line B, data is encoded into binary ones and zeros by employing a bilevel pulse signal having a pulse to pulse repetition period of 3 ms. A pulse width of 1 ms indicates a binary "0" while a pulse width of 2 ms indicated a binary "1". For IR transmission from the telemetry head, the high portions of the binary signal correspond to intervals when the IR drive is enabled and the light emitters are lit. For the resonant transponder 30 of FIG. 2 the high portions of the pulse width modulated binary data signal correspond to intervals when the shunt transistor is conductive.

Figure 6:
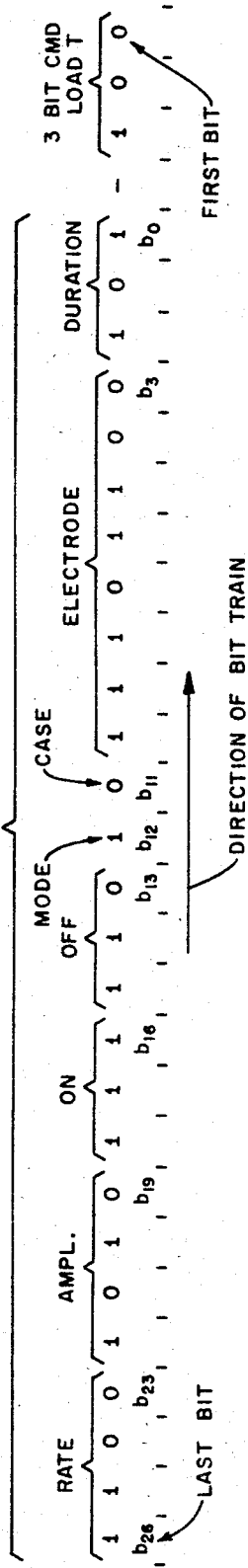
FIG. 6 illustrates a typical pattern of serial bits for the load command followed by a data word.

The programmer console 12 converses with the implant by means of two different kinds of words: a 3-bit command word and a 27-bit parameter value data word, as illustrated in FIG. 6. The command words call corresponding subroutines on the ROM 52. The commands per se are not stored in the microprocessor 50; they are directly acted upon. The 27-bit data word, on the other hand, contains all of the pulse parameter data and is stored in the microprocessor 50. Among the 16 scratch pad registers in the microprocessor (CDP1802), two pairs of registers are chosen as temporary and control registers for the parameter data word transmitted by the programmer 12. The first pair of registers is designated temporary register A (TEMPA) and temporary register B (TEMPB). Each has a 16-bit capacity for a combined total of 32 bits, five fits of which are dedicated to a fixed model identification number. The second pair of registers is designated control A (CONTA) and control B (CONTB) in the same manner. The remaining register assignments are discussed in conjunction with Appendix I.

Figure 7:
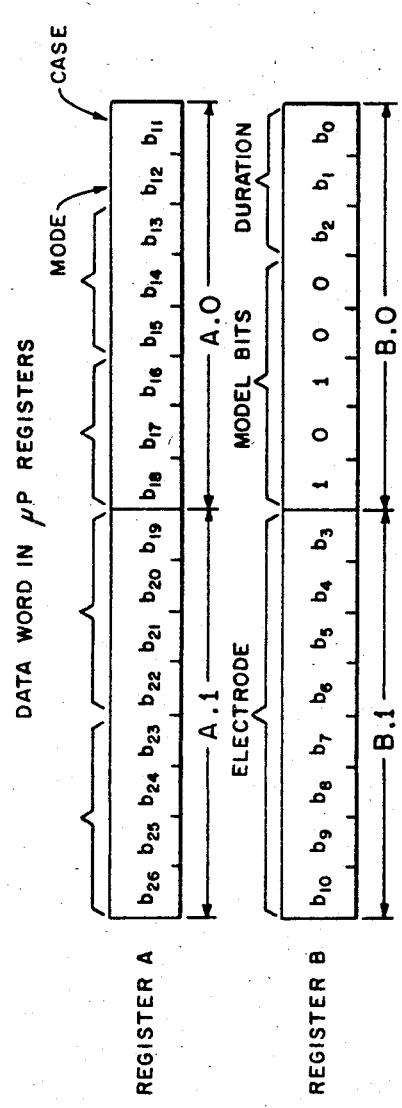
FIG. 7 is a diagram of bit positions of the data word in a pair of registers on the microprocessor chip.

The command vocabulary includes the following commands designated by six corresponding 3-bit codes: LOAD T, ACTIVE, XMIT T, XMIT C, ROM DMP, and STAT OFF. The command LOAD T signals the microprocessor to place the immediately following 27 bit data word into the temporary registers A and B as shown in FIG. 7. The data word comprises 27 serial bits which are position coded. The first three bits beginning with b0 dictate the pulse duration by reference to a stored parameter table in the ROM 52. The next eight bits beginning with bit position b3 define the electrode connections (off, anode, cathode, i.e., two bits for each of four electrodes). The next bit, bit position b11, indicates whether the case will start off as an anode or will be disconnected. Bit b12 selects constant or alternating polarity mode of operation. The next three bits beginning with bit position b13 establish the off time for a pulse train mode of operation, and the following three bits beginning with b16 specify the on time. The on/off times each may be zero to seven minutes long in one minute increments and are actually given in the parameter table. The four bits beginning with b19 denote the amplitude of the output current and the last four bits, b23–b26 designate the programmed pulse rate. The amplitude and rate bits also refer to the parameter table.

Figure 8:
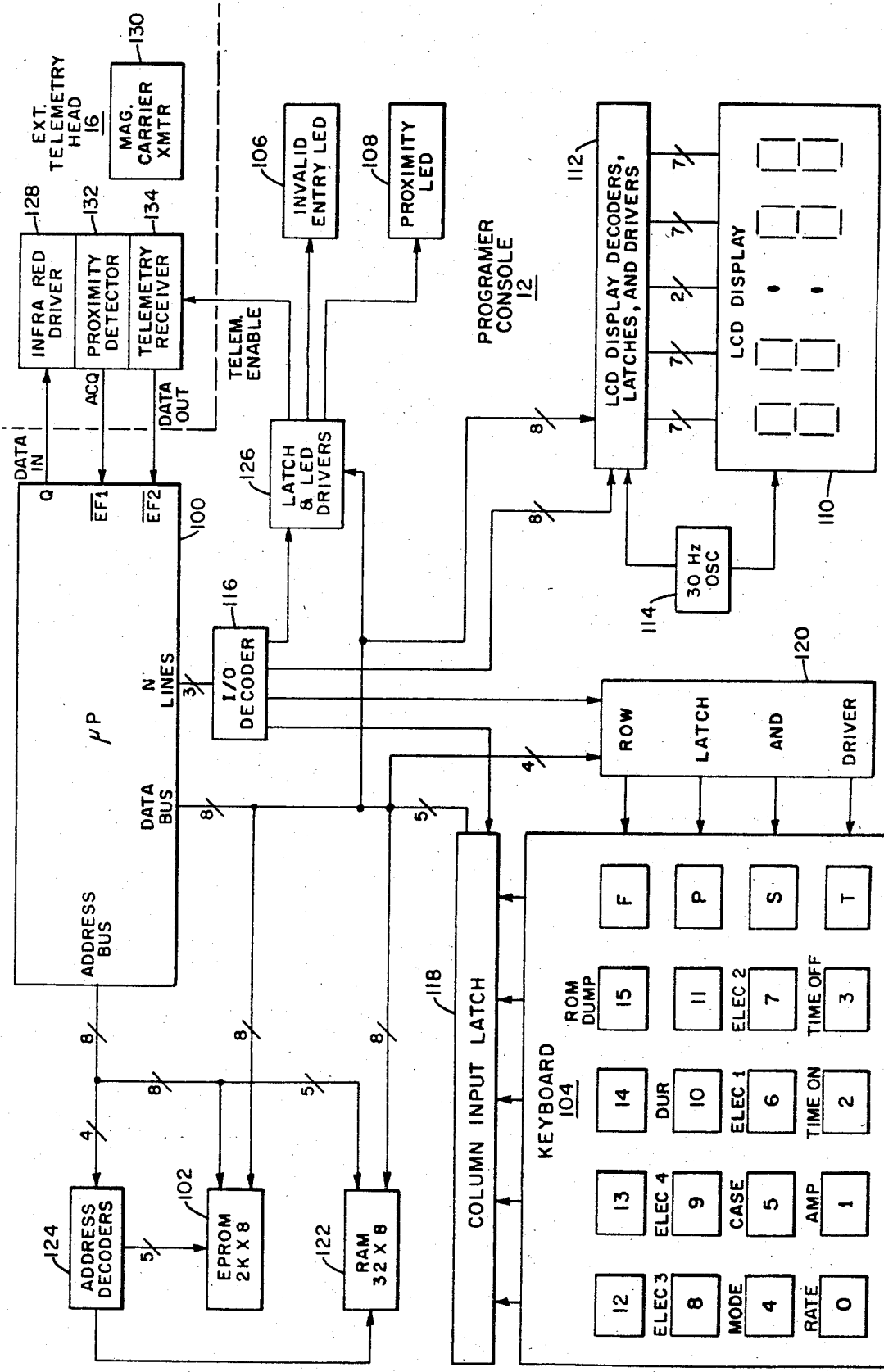
FIG. 8 is a block diagram of the programmer console and telemetry head of FIG. 1.

The implanted stimulator 10 can be interrogated and reprogrammed to new pulse parameters by means of an interactive external neural stimulator programmer, as shown in FIG. 8. The programmer is an intelligent, microprocessor-based interactive system capable of noninvasively programming, interrogating and verifying the parameter values in the neural stimulator implant 10. The programming system comprises two separate components: a table-top programmer console 12 and a cable-connected hand-held telemetry head 16, described in detail in the incorporated copending application by Slocum et al. The programmer console 12 is run by a single chip CMOS 8-bit microprocessor 100 of the same type as microprocessor 50 in the implant, i.e. the RCA CDP 1802. Software is stored on an electronically programmable read only memory (EPROM 102).

The console 12 includes a twenty key calculator-type keyboard 104 for parameter selection, review and programming by the operator. The keyboard 104 consists of four command keys in the right hand column bearing the letters F, P, S and T and 16 numeric keys (0–15) arranged in a 4×4 array. The numeric keys 0–10 are marked with legends corresponding to the various programmable parameters duch as rate, amplitude, etc. Key number 15 bears a legend ROM DMP. Briefly, the "S" key is used to program the implant to the off condition automatically; the "P" key programs the stimulator to new pulse parameter values; the "F" key is used to propose a new value for any one of the programmable parameters; and the "T" key merely displays the already proposed value for the selected parameter.

Adjacent to the keyboard 104, a pair of visible light emitting diodes (LED's) 106 and 108 are connected to indicate, respectively, an invalid keyboard entry and proximity of the programming head 16 to the implant 10. Also adjacent to the keyboard 104 is a four digit, seven segment LCD clock-type display 110 operated by conventional decoder, latch and driver circuitry 112 and a 30 hertz oscillator 114. The display 110 is controlled via an I/O decoder 116 responsive to the three N command bits from the microprocessor 100. Data to be displayed is taken off of the 8-bit data bus. The keyboard 104 is interrogated via the I/O decoder 116 which controls a column input latch 118 and row latch and driver circuit 120. Key rows are individually interrogated by the row latch and driver circuit 120 and the keyed information is put on the data bus via the column input latch 118. A 32-byte random access memory (RAM) 122 is used for temporary storage of current and proposed parameter data words. The EPROM 102 and RAM 122 are both accessed by an address decoder circuit 124 via the microprocessor address bus. Incoming and outgoing data from the memories 102 and 122 is placed on the data bus. The command bit I/O decoder 116 in conjunction with the data bus also operates the telemetry enable output and LED's 106 and 108 via latch and LED drivers 126.

The telemetry head 16 performs receiving, transmitting and proximity detecting functions. For signalling into the implant 10, the head 16 includes an infrared driver 128 which operates a plurality of infrared LED's (not shown) located on the surface of the head 16. The infrared driver 128 is keyed directly by the serial bit Q output of the microprocessor 100 in the console 12. The Q output is provided in pulse width modulated form (i.e., 1 ms and 2 ms pulses), and the driver 128 turns the IR LED's on and off in accordance with the state of the Q output. Inside the implant 10 this data signal is received by the IR receiver circuit 36 shown in FIG. 2.

The telemetry head 16 also includes a 16 kHz magnetic carrier transmitter 130 for flooding the implant 10 with a continuous wave myriametric frequency magnetic signal. The reflected or reradiated magnetic signal from the implant 10 is picked up with a characteristic phase shift. The amplitude of the phase shift is threshold detected by a proximity detector 132. The output ACQ of the detector 132 sets an external flag at input (EF1)-bar of the microprocessor 100 to indicate that the programming head 16 is adequately positioned with respect to the implant 10 to carry on two-way communication. A telemetry receiver 134 in the head 16 produces an output signal to the (EF2)-bar input of the microprocessor 100. The output of the receiver 134 duplicates the pulse width modulated binary data signal applied to the resonant transponder circuit 30 (FIG. 2) in the implant. The phase shift caused by shunting the tuned coil in the implant is demodulated by the receiver 134. The telemetry enable signal from the console 12 activates the receiver 134 when the external programmer is expecting a data transmission from the implant.

The software program stored on EPROM 102 which operates the programming system is reproduced in FIG. 11 and Appendix III with an accompanying English language flow chart in Appendix IV. Appendix III contains not only the machine code in hexadecimal digit form but also fully annotated assembly language. This material, like that for ROM 52 of the implant, is based on the standard programming repertoire of the RCA CDP 1802.

When the programmer is turned on, before the keyboard comes into play, the software runs the programming system through an automatic initial interrogation routine outline in twenty-six steps in Table I below.

TABLE I

| Initial Interrogation Routine | |
|---|---|
| PROGRAMMER ACTION | STIMULATOR RESPONSE |
| 1. Wait for proximity detection. | 2. Enable infrared detector. |
| 3. Transmit "REQUEST TO SEND" pulse and wait for "CLEAR TO SEND" pulses. | 4. Transmit 2 "CLEAR TO SEND" pulses. |
| 5. Transmit "INTERROGATE CONTROL | 6. Decode Command. |

TABLE I-continued
Initial Interrogation Routine

| PROGRAMMER ACTION | STIMULATOR RESPONSE |
|---|---|
| REGISTER" Command | |
| | 7. Transmit contents of Control Register. |
| 8. Decode Control Register Pulse Train. | |
| 9. Store control register values. | |
| 10. Wait for Proximity detection. | |
| 11. Transmit "REQUEST TO SEND" pulse and wait for "CLEAR TO SEND" pulses. | 12. Transmit 2 "CLEAR TO SEND" pulses. |
| 20. Transmit "INTERROGATE TEMPORARY REGISTER" command. | 21. Decode command. |
| 23. Decode temporary register pulse train. | |
| 24. Store temporary register values. | |
| 25. Compare temporary register values to control register values. Go to Step 1 if not equal. | 26. Resume stimulation. |

On power up, the programmer clears the display 110 and waits for the programming head 16 to be placed over the implant. Once the programmer detects proximity via the ACQ line, the programmer lights the proximity indicator LED 108 and proceeds to interrogate and verify the implanted stimulator's current programmed values, i.e. the values stored in the control registers A and B of the microprocessor 50 inside the implant. Meanwhile, in the implant the 16 kHz magnetic field enables the infrared detector 36 (FIG. 2).

Once proximity is detected, an automatic "handshaking" interaction occurs as shown in FIG. 9. The upper line in FIG. 9 represents IR transmission via the infrared driver 128 in the head 16. The lower line represents the output of the telemetry receiver 134 which receives the phase shift modulated data signal from the implant, as described in the copending application. According to step 3 of Table I, the programmer generates at least one request to send pulse. The first IR pulse detected by the implant signals EF1 in microprocessor 50 of FIG. 3. This condition is continuously tested in the implant by the operating cycle of the microprocessor 50. In response to EF1, the software in the implant causes the serial Q output of the microprocessor 50 to be set to "1" for 1 ms, to "0" for 2 ms and again to "1" for another 1 ms pulse. These two pulses from the implant (lower line, FIG. 9) represent "clear-to-send" pulses to complete the handshake routine. The programmer will automatically continue to generate request-to-send pulses every 7 ms until detection of clear-to-send pulses from the stimulator.

Next, in step 5 of Table I, the "interrogate control register" command, i.e., the 3-bit XMIT C command "001", is transmitted by IR pulses. The stimulator decodes the command with software and then transmits the 32-bit contents of the dual control registers in the implanted microprocessor 50, as shown in FIG. 9. The contents of the control registers are shifted serially out the Q output of the implanted microprocessor in pulse width modulated code and trasmitted via the resonant transponder to the external head 16. Software in the programmer console 12 decodes the control register pulse train (step 8) and stores the control register values (step 9).

At this point the automatic initial interrogation routine repeats the handshaking routine in steps 10, 11 and 12 after which the programmer transmits the 3-bit LOAD T command followed by the serial contents of the stored control register values which were previously transmitted in step 7 from the implant. Steps 14 and 16 in the stimulator cause the externally stored control register value to be placed in the temporary registers A and B in the microprocessor 50 of the implant. At this point, the current values of the actual stimulation parameters in the control registers have been transferred to the temporary registers so that now the temporary and control registers in the implant should both be identical with the values received and stored by the external programmer.

Steps 17 through 19 repeat the handshaking routine once again to insure continuing proximity for proper signal acquisition. In step 20 the programmer causes 3-bit XMIT T command to be transmitted via the IR driver 128, which makes the stimulator transmit out the contents of its temporary registers. Temporary register values are stored externally in the RAM 122 and compared in steps 24 and 25 to the previously stored control register values. If they match, successful interrogation is indicated to the operator by four dashes in the digit positions of the LCD display 110: [-:-]. If the values do not match, the entire interrogation routine is repeated. In the meantime, in the absence of unexecuted external commands, the stimulator resumes stimulation.

The automatic initial interrogation interaction of Table I is a data transfer checking routine. Thus, the implant transfers a 32-bit word to programmer; the programmer transfers the same 32-bit word back to the implant and then asks the implant to transfer the same 32-bit word back to the programmer which compares it with the original reception to see if the two match. This interplay insures the transmission and decoding integrity of the communications system.

Once the initial interrogation routine is successfully completed, software turns off the proximity indicator LED 108 and begins monitoring the keyboard. However, the contents of the control registers in the implant are maintained in storage (RAM 122) reflecting the current parameters which were found to be in effect for the implant during the initial interrogation routine. Table II below indicates the display reference numbers corresponding to the programmable values which may be selected via the keyboard 104.

TABLE II

| Parameter | Display Ref. # | Actual Value |
|---|---|---|
| Rate | 0 | 8 pps. |
| | 1 | 10 pps. |

TABLE II-continued

| Parameter | Display Ref. # | Actual Value |
|---|---|---|
| | 2 | 12 pps. |
| | 3 | 15 pps. |
| | 4 | 20 pps. |
| | 5 | 25 pps. |
| | 6 | 30 pps. |
| | 7 | 33 pps. |
| | 8 | 40 pps. |
| | 9 | 50 pps. |
| | 10 | 60 pps. |
| | 11 | 75 pps. |
| | 12 | 100 pps. |
| | 13 | 120 pps. |
| | 14 | 150 pps. |
| | 15 | 200 pps. |
| Amp (Amplitude) | 0 | 0.1 ma. |
| | 1 | 0.2 ma. |
| | 2 | 0.4 ma. |
| | 3 | 0.6 ma. |
| | 4 | 0.8 ma. |
| | 5 | 1.0 ma. |
| | 6 | 1.2 ma. |
| | 7 | 1.4 ma. |
| | 8 | 2.0 ma. |
| | 9 | 3.0 ma. |
| | 10 | 4.0 ma. |
| | 11 | 5.0 ma. |
| | 12 | 6.0 ma. |
| | 13 | 7.0 ma. |
| | 14 | 8.0 ma. |
| | 15 | 10.0 ma. |
| Ton (Time On) | 0 | 0 min. |
| | 1 | 1 min. |
| | 2 | 2 min. |
| | 3 | 3 min. |
| | 4 | 4 min. |
| | 5 | 5 min. |
| | 6 | 6 min. |
| | 7 | 7 min. |
| Toff (Time off) | Same as Ton | Same as Ton |
| Mode | 0 | Continuous |
| | 1 | alternate |
| Case | 0 | off |
| | 1 | anode |
| Elec 1 (Electrode 1) | 0 | anode |
| | 1 | off |
| | 2 | invalid |
| | 3 | cathode |
| Elec 2 (Electrode 2) | Same as Elec 1 | Same as Elec 1 |
| Elec 3 (Electrode 3) | Same as Elec 1 | Same as Elec 1 |
| Elec 4 (Electrode 4) | Same as Elec 1 | Same as Elec 1 |
| Dur (Duration) | 0 | 50 sec. |
| | 1 | 100 sec. |
| | 2 | 150 sec. |
| | 3 | 200 sec. |
| | 4 | 250 sec. |
| | 5 | 300 sec. |
| | 6 | 350 sec. |
| | 7 | 400 sec. |

The "F" command key calls a subroutine which is used to display the current value and propose a new value for any one of the programmable parameters listed above the numeric keys 0–10. Depressing the "F" key displays a "−4" on the left half of the display.

EXAMPLE 1

| Key Press | Resulting Display |
|---|---|
| F | [−4: ] |
| 1 (amp) | [1:10] |

The above two keystroke sequence, F, 1, results in the display of the current value for the amplitude according to the stored contents of the control registers. The "1" on the left half of the display corresponds to the numeric key above which is written "amp" for amplitude on the keyboard 104 of FIG. 8. The "10" on the right half of the display is a reference number for the value 4.0 ma from the parameter Table II above. To propose a new value, a third consecutive key strike, "9", for example, results in a display [1:9]. The "1" still represents the parameter amplitude, and the "9" represents the proposed new value corresponding to 3.0 ma, which is now maintained in storage by the programmer console 12.

This operation is repeated for each of the other parameters, RATE, TIME ON, TIME OFF, MODE, CASE, ELECTRODES 1, 2, 3 and 4, and DURATION (pulse width). Initially, however, the register in the external programmer which is to hold the proposed values is set equal to the current values received from the implanted control register. Accordingly, only those parameters which are desired to be changed have to be entered via the "F" key sequence.

After the new parameter values have been entered, the "P" command key is used to program the implant to the new proposed value "P". Depressing the "P" key clears the display until verification of successful programming is indicated by the appearance of "−3" in the left half of the display: [−3: ]. A step by step description of the programming routine initiated by striking the "P" key is presented in the following Table III.

TABLE III

Programming Routine

| PROGRAMMER ACTION | STIMULATOR RESPONSE |
|---|---|
| 1. Wait for proximity detection. | 2. Enable infrared detector. |
| 3. Transmit "REQUEST TO SEND" pulse and wait for "CLEAR SEND" pulses. | 4. Transmit 2 "CLEAR TO SEND" pulses. |
| 5. Transmit "INTERROGATE CONTROL REGISTER" command. | 6. Decode command. |
| 8. Decode control register pulse train. | |
| 9. Compare redeived "Control Register" data to previous "Control Register" data. If not equal programmer assumes new patient and goes to Step 1 of Table I. | |
| 10. Wait for proximity detection. | |
| 11. Transmit "REQUEST TO SEND" pulse and wait for "CLEAR TO SEND" pulses. | 12. Transmit 2 "CLEAR TO SEND" pulses. |

TABLE III-continued
Programming Routine

| PROGRAMMER ACTION | STIMULATOR RESPONSE |
|---|---|
| 13. Transmit "LOAD TEMPORARY REGISTER" command. | 14. Decode command. |
| 15. Transmit "PROPOSED VALUES". | 16. Decode pulse train and store in Temporary Register. |
| 17. Wait for proximity detection. | |
| 18. Transmit "INTERROGATE TEMPORARY REGISTER"" command. | 21. Decode command. |
| | 22. Transmit contents of Temporary Register (Proposed Values). |
| 23. Decode and Store Temporary Register pulse train values. | |
| 24. Compare Temporary Register values to Proposed Values. Go to Step 1 (Table III) if not equal. | |
| 25. Wait for proximity detection. | |
| 26. Transmit "REQUEST TO SEND" pulse and wait for "CLEAR TO SEND" pulses. | 27. Transmit 2 "CLEAR TO SEND" pulses. |
| 28. Transmit "ACTIVATE" command. | 29. Decode command. |
| | 30. Transfer Temporary Register values to Control Register. |
| 31. Wait for proximity detection. | |
| 32. Transmit "REQUEST TO SEND" pulse and wait for "CLEAR TO SEND" pulses. | 33. Transmit 2 "CLEAR TO SEND" pulses. |
| 34. Transmit "INTERROGATE CONTROL REGISTER" command. | 35. Decode command. |
| 37. Decode and store Control Register values. | |
| 38. Compare received Control Register values to Proposed values. Go to Step 1 (Table III) if not equal. | 39. Resume stimulation. |

The first eight steps of the automatic sequence activated by pressing the "P" key are the same as in the initial interrogation routine in which the contents of the implant control registers are transmitted out to the programmer after proximity detection and handshaking. This time, the programmer compares the newly received control register data to the previously stored control register data which was taken during the initial interrogation. If the two do not match, the programmer assumes that there is a new patient and runs through the initial interrogation routine of Table I. This is indicated, assuming that the initial interrogation is successful, by four dashes appearing in the digit positions of the display [-:-]. If the contents of the control register match in step 9 of Table III, the programming routine goes through acquisition and handshaking again and then commences loading the temporary registers in the microprocessor 50 of the implant by transmitting the 3-bit command LOAD T followed by the 27-bit data word.

The programming routine reacquires and handshakes again in steps 17-19 and interrogates the just loaded temporary registers by issuing a 3-bit command XMIT T. In steps 23 and 24 the temporary register values transmitted out by the implant are compared to the proposed values and if they do not agree the programming routine in Table III starts over. If they agree, the programmer reacquires, rehandshakes with the implant (steps 25-27) and transmits the ACTIVE command which makes the implant transfer the values in the temporary registers to the control registers (step 30). This command reprograms the stimulator to the desired parameter values as explained below in conjunction with the stimulator software. However, the external programming routine is not finished yet. After rehandshaking, it orders the implant to transmit the control register values by sending the 3-bit command XMIT C, as in the initial interrogation routine. If the just transmitted control register values do not equal the proposed values still stored in the external programmer, the programming routine is started over. If they are correct, the display flashes [-3:] signalling the end of the programming routine and the resumption of stimulation by the implant according to the newly programmed stimulation parameters.

There are two other functions which can be selected by the programming keyboard 104. The "T" command key is similar to the "F" command key but is used to display only the proposed value of the selected parameter.

EXAMPLE 2

| Key Press | Resulting Display |
|---|---|
| T | [-1:] |
| 1 | [1:9] |

The above two keystroke sequence displays the proposed value for amplitude which was entered in the first example. If the "F" key were used instead of the "T" key, the value for the amplitude parameter which was found during initial interrogation (i.e., "10") would have been displayed.

The "S" command key is used to program the implant to "OFF" automatically without having to use the F key to enter all of the OFF conditions as proposed new values. Depressing the "S" key is indicated by displaying a "−2" in the left half of the display.

In addition to the four commands described, the programmer is capable of verifying the read only memory contents of the implant. This feature would generally only be available in a programmer used in manufacturing to verify the ROM contents of the implantable stimulator before shipping. This feature is available through the following key stroke sequence:

EXAMPLE 3

| Key Press | Resulting Display |
|-----------|-------------------|
| F         | [−4: ]            |
| 15        | [15: ]            |

The machine cycle of the external microprocessor 100 is by design about 1.25 microseconds. Thus the crystal clock for the external microprocessor 100 should be nominally 6.5 megahertz. Since the implanted and external devices operate with independent power supplies and the internal clock at least by present design is not a crystal oscillator, it is possible with aging batteries for the timing of the telemetry pulse code to elude the 1.5 ms sampling interval. Thus it may be advisable to test the pusle width of the clear to send pulses for example and adjust the sampling interval accordingly with additional software.

The ROM DMP and STAT OFF commands from the external programmer call specific subroutines in the implant. The ROM DMP subroutine automatically dumps the serial contents of the implanted ROM 52 out the data port Q of the microprocessor 50 in pulse width modulated code. The STAT OFF subroutine in the implant automatically establishes off parameters directly via an internal initialization subroutine on the ROM 52.

Appendix I contains the program listings in machine code and assembly language for the implanted microprocessor 50 along with English annotations. Appendix II is a detailed flow chart of the routines in assembly language with English comments. The software is based on standard CDP1802 architecture and standard CDP1802 instruction repertoire. However, the program is considerably more complex than the external programmer software (Appendix III). Thus, the explanation which follows is tied more closely to the actual software instructions.

In the Appendices the higher order byte in a 16-bit rate register is specified as R(RATE) 0.1, for example. The lower order byte in the TEMPA register is specified as R(TEMPA) 0.0. The address of the decode subroutine, a specific number, is specified as A(DECODE).

In Appendix I the first column on the left comprises four hexadecimal (hex) digits indicating memory locations for the instructions in the second column, which are also given in hex digit form. Each pair of hex digits represents one 8-bit byte in the ROM. The four decimal digits in the third column designate line numbers of the printout. For example, in line 33 there are five instruction bytes located in consecutive memory addresses 2, 3, 4, 5 and 6. The next column to the right of the line number column includes program location markers such as "START" which form headings to identify special locations in the program. The next column gives the assembly language translation of the machine code instruction, and finally the English annotations are provided in the far right portion of each line set off from the assembly language by a pair of periods.

The instructions in the second column of Appendix I are stored in ROM 52 (FIG. 3) which is appropriately programmed by mask during manufacture. The program takes up just over two pages of consecutive memory locations (205 hex). Unused ROM locations contain zeros. Seventy-nine more locations (03B1to 3FF) for the parameter tables are listed beginning at line number 484. Here, specific alternative values for on times, off times, rates, current amplitudes and pulse durations are addressed by corresponding portions of the data word. The actual rate for example is not specified by the rate bits of the data word. Instead, the rate bits give the local address in the table where the desired rate can be obtained. Different parameters can be prescribed in the ROM tables without affecting the program operation or data word. This feature enables the physician to bring several neural stimulator packages into the operating room, each one different from the other only in terms of the ROM parameter tables, to provide an even wider selection of parameters than is afforded by a single programmable neutral stimulator. Once implanted, of course, the neural stimulator of this embodiment would be confined to the sixteen selectable rates in the parameter table for the ROM in that specific neural stimulator. The parameter table feature also provides product adaptability for the manufacturer.

The first 26 line numbers of the program listing in Appendix I define the assignments for the 16 scratch pad registers in the microprocessor 50. The register numbers are arbitrary. TEMPA, TEMPB and CONTA and CONTB are the 16-bit temporary and control registers which receive the data word. Registers ONE, MAIN, RDEC and FREE are general utility registers. The RATE register holds the programmed rate from the parameter table for quick reprogramming during on/off cycles. There are two registers each for the case and electrode connections for alternating polarity operation on consecutive output pulses. The on/off register indicates which portion of the cycle the neural stimulator is presently in.

The program actually begins at line number 29 where the interrupt capability of the microprocessor is disabled. When the interrupt is disabled, stimulator output pusles are also disabled because the microprocessor cannot issue an I/04 output pulse. The registers are initialized by placing the address of the first interrupt service subroutine in register ONE, the address of the DECODE subroutine in register RDEC and the address of the telemetry output subroutine "SUBQ" in register QOUT. Next the STAT OFF subroutine automatically places preordained bit patterns in the temporary registers A and B. The STAT OFF subroutine programs parameter values which cause the neural stimulator to be in the off condition. In addition to the STAT OFF parameters the five higher order bits in the lower order byte of temporary register B are assigned model number bits whih identify the neural stimulator model.

Next the program branches to the ACTIVE subroutine which begins at line 211 of Appendix I. The ACTIVE routine moves the contents of the temporary registers into the control registers and programs all of the neural stimulator's parameters. Before transferring the data to the control registers, the microprocessor first programs the amplitude latch by isolating the amplitude code in the higher order byte of the temporary register A, obtaining the addressed amplitude from the parameter table and putting it on the data bus. The assembly language instruction "INP 3" activates the I/03 strobe line and sets the reed switch flip-flop 42 in the communications module (FIG. 2). After programming the amplitude latch, the entire contents of the temporary registers are transferred to the control registers. The rate and lower order duration latches 70 and 80 are programmed in a similar manner using the code from the corresponding portion of the control register to address the parameter table. The higher order duration bits are placed in the case registers for subsequent programming.

The electrode and case registers are programmed in lines 256 through 303 beginning at location 31 in Appendix I. The eight electrode polarity bits are placed in the lower order bytes of the two electrode registers (ELEC1 and ELEC2) and the mode bit is tested. If the mode of operation is to be continuous there is no need to change the bits in the second electrode register. However if the mode indicates alternating polarity, the bits in the second electrode register (i.e., for the even cycles) are logically manipulated to produce the alternate mode. This is somewhat more complicated than merely taking the complement of the bits since the two bit code for each electrode can specify four different conditions, only two of which are reversible, that is anode and cathode. The other two are of (i.e., disconnected) and disallowed, both of which remain the same on odd and even cycles.

At location 33 the case is programmed by first testing the case bit. Only the two higher order bits of the lower order byte of the two case registers (CASE1 and CASE2) are used. If the case is always off, "1" and "0" are placed in the higher order bits of both registers. If the case is normally connected as an anode then zeros are placed in the higher order bits of both registers if the mode is continuous. If alternate, zeros are placed in the higher order bits of the first case register and ones are placed in the higher order bits of the second case register.

The subroutine beginning at location 38 (line 308) programs the correct on and off times into the corresponding registers by isolating the on and off code from the control register. If the on time code indicates that the stimulator is to be always off then the pulse rate is slowed down to the minimum by the subroutine beginning at location 61. On the other hand, if the code for the off time indicates that the stimulator is supposed to be always on, the subroutine beginning at location 60 reprograms the rate latch via the I/01 line and enables the interrupt to allow the neural stimulator to begin operating. In either case, always on or always off, there is no need for the microprocessor to time the on/off cycle. Accordingly, the program at location 62 allows the interrupt line to remain either disbled or enabled depending on whether the stimulator is supposed to be always off or always on while the software continuously tests EF1 to see whether it is time to program. Otherwise, the microprocessor is exclusively under the control of the itnerrupt request input, i.e., the output of the rate counter.

A more complicated operation takes place if on and off times are involved. To continue with the routine which began at location 38 in line 319, the off time from the parameter table addressed by the off code in the data word from the control register is placed in the higher order byte of the OFF register and the hex digits 6 and 5 are placed in the lower order byte of the OFF register in order to get closer to 60 seconds. Next the on code bits are isolated and placed in the FREE register. The CYCLE register is pointed to the proper position in the on parameter table. The on parameter tables run from memory locations 3B1 through 3CF. Each on value in the table is two bytes long. The table is addressed by obtaining the higher order address byte (03) of the parameter tables and adding to it the doubled rate number. Next the value in the on time code number and the product is subtracted from hex digits FFFF and stored in the ON register. The program then branches to location 42 (line 132) to set up the on time by placing the contents of the ON register into the CYCLE register, reprogramming the stimulator rate and setting the ON/OFF flag register to on, whereupon the program returns to the starting point of the MAIN routine at location 21 (line 47).

The MAIN routine enables the interrupt line and tests EF1 to see whether it is time to program. If not, on each pass through the loop the program repeatedly increments the number in the cycle counter until the cycle counter times out. When the cycle counter is at zero, the interrupt is disabled and the program shifted to location 41 which tests the on/off register. If the stimulator has been on and is going to be turned off, the RATE latch is programmed to the minimum rate and the contents of the OFF register are placed into the CYCLE register and the off flag set. After the off flag is set the software returns to location 23 by bypassing the enable interrupt instruction and continues to test EF1 and increment the cycle counter. On the other hand if the stimulator has been off and is going to be turned on the contents of the ON register are placed in the CYCLE register and the programmed rate is reprogrammed. After the on flag is set, the program returns to the top of the MAIN loop (location 21) and enables the interrupt which allows the stimulator output to resume.

The remainder of the routines in the program are callable subroutines for performing special tasks. The most important of these of course is the interrupt service subroutine (line 435) which occurs whenever the rate counter 72 times out and interrupt is not disabled. In the interrupt subroutine the case polarity and higher order duration bits are programmed by applying the contents of the CASE1 register to the MA bus lines while strobing I/05. Next, the contents of register ELEC1 are put on the memory bus while strobing I/04. The address of the interrupt service routine is incremented so that the next time the interrupt occurs the second or alternate interrupt service subroutine will be called. In the second interrupt subroutine, the contents of the CASE2 register are placed on the bus while the I/05 line is strobed. Next the contents of register ELEC2 are applied to the memory address bus and the I/O line 4 is strobed to program the electrode polarity and enable the output circuit. If the alternating mode has been selected, the connections for the case and electrodes which have been connected as either anode or cathode are reversed.

The other subroutines perform special tasks in decoding or telemetry. The COMMAND subroutine beginning at line 65 decodes the 3-bit command code and steers the program accordingly. The command subroutine is also responsible for generating the 1 ms clear to send pulse in response to the first programming pulse when EF1 is set and 2 ms later for generating a second 1 ms pulse (ready-to-program) after which the decode subroutine is called to test the status of (EF2)-bar, i.e., the IR data input. The XMIT T (line 169) and XMIT C (line 177) subroutines shift the contents of the temporary or control register, respectively, out the Q output port for telemetry back to the programmer. The SUBQ subroutine shifts the "D" register (i.e., the "accumulator" in the microprocessor) out the Q output of the microprocessor, pulse width modulated. The 27 pulse train decoding routine beginning at line 187, location 1, decodes the twenty-seven pulse width modulated input signals into ones and zeros and stores the results in temporary registers A and B. Finally, the DECODE subroutine (line 404) tests each bit at 1.5 ms to determine whether it is a zero or a one. The DECODE subroutine is incorporated in the COMMAND subroutine and the 27 pulse train decoding subroutines.

OPERATION

If the programmed on/off cycle of the implanted stimulator is such that the stimulation pulse train is always on (i.e., off time equals zero), the microprocessor 50 spends all of its free (non-interrupt) time executing the instruction at location 62 (line 356). This instruction causes the microprocessor to keep on testing EF1 to see if it is time to program. When responding to an interrupt request the microprocessor executes the interrupt service subroutines. If the programmed on/off cycle is such that the stimulator is always off (i.e., on time equals zero) the microprocessor spends all of its time testing EF1. If the stimulator is executing a real on/off duty cycle, the microprocessor repeatedly tests EF1 and increments the cycle register, spending all of its time at location 23 (line 50). In transition from one state to the other, the microprocessor executes instructions beginning at location 41 and then returns to the timing and EF1 testing loop at location 23. While in this loop, the microprocessor will respond to interrupt requests only in the on portion of the cycle.

When the physician wants to change the programmed pulse parameters to prescribe a different stimulation therapy program for the patient, he positions the telemetry head 16 over the implant with the magnetic carrier transmitter 130 (FIG. 8) on, as described in the above-referenced copending application. The resonant transponder 30 (FIG. 2) turns on the IR receiver 36. The first IR pulse transmission from the telemetry head sets EF1 in the microprocessor 50. EF1 disables the interrupt (location 22) and calls the command decoding routine which sends the two "clear to send" pulses back to the telemetry head via the transponder 30, and then waits for a command. The programmer console automatically executes the initial interrogation routine (Table I). The thirty-two bit data word received by the telemetry head receiver 134 is decoded and stored externally. Meanwhile the implanted microprocessor returns to normal operation via location 38 (line 308). The physician can display the current parameters one at a time with the "F" key and respective number keys.

After selecting new parameters for stimulation via the "F" key strike sequence, the physican initiates the automatic programming routine of Table III by pressing the "P" key. After the "handshake" routine, and patient confirmation, the temporary registers are loaded and verified before transfer to the control registers. After executing each external command, the microprocessor returns to normal operation via location 38 (Appendix I). The ACTIVE command calls the subroutine which transfers the contents of the temporary registers to the control registers and reprograms all of the latches and the RATE, ON, OFF, ELEC1, ELEC2, CASE1, and CASE2 registers in the microprocessor and then returns to normal operation with the newly programmed parameters via location 38. To double-check, the external programming routine interrogates the control registers once more via the XMIT C command. Following telemetry execution of the XMIT C subroutine, normal operation continues via location 38.

If, prior to reprogramming, the patient has turned off the stimulator by disabling the slow clock 54 with his reed switch permanent magnet, the fast clock will operate the microprocessor through a portion of the reprogramming schedule in the following manner. When the telemetry head is placed over the implant, the passive tuned coil transponder activates the IR receiver. The first IR pulse resets the EF1 flip-flop 74 (FIG. 3), turning on the fast clock. The slow clock remains off. The registers are interrogated with the fast clock operating the microprocessor. No stimulation pulses (interrupt requests) will occur until the slow clock starts. To start the slow clock the magnet can be used to toggle the read switch flip-flop 42. Altnernatively, the flip-flop is reset by reprogramming the latches. In the ACTIVE routine, the amplitude latch is first programmed via I/03 (line 220), which also sets the reed switch flip-flop 42 thus starting the slow clock and the rate counter immediately. As the ACTIVE routine continues, the rate latch is programmed via I/01 (line 235) which is also fed back to set the EF1 flip-flop. The Q output of the EF1 flip-flop 74 operates the clock multiplexers which (normally) direct the slow clock to the microprocessor and disable the fast clock. From this point on, the ACTIVE routine operates at the slow clock rate in the normal fashion until normal operation of the stimulation pulse generator is resumed via location 38.

The microprocessor-controlled neural stimulator implant described above optimizes the flexibility of control over the stimulation pulse parameters for the manufacturer as well as the physician while minimizing the number of components and current drain for a long battery life. Energy is conserved by disabling the fast clock which times the pulse width except when absolutely necessary for this function or for operating the microprocessor. The full two-way communication capability of the implant assures reliable program entry and offers a channel for interrogating the operating parameters of the stimulator at any time. The unique division of labor between the stored program microprocessor and the discrete digital counter offers maximum flexibility and efficiency. The alternating polarity mode of operation is a formerly unavailable stimulating mode which will have physiological advantages in certain situations. In particular, it is believed that electrochemical effects on the tissue at the site of the electrode will be ameliorated by alternating polarity for extended therapy. The use of a stored parameter table for rate, width, amplitude and on and off times adds the capability of altering the stored parameters by mask without any effect on the operating system.

The above-described circuitry can be varied and modified in many respects without departing from the underlying principles of the invention. For example, the operation of the microprocessors does not depend on any specific form of data transmission. While pulse width modulated IR transmission and reflected signal magnetic telemetry are preferred, other modes of communication will work if the system is adapted to decode the data. The RCA CDP1802 microprocessor is preferred for the implant because of its CMOS construction and abundance of internal registers. Nevertheless, other commercially available microprocessor systems can be used, and with advances in technology, new components will undoubtedly be even better suited. External random access memory can be used if needed. The slow and fast clocks can be implemented in a variety of different ways although the RC Schmitt trigger combinations illustrated in FIG. 3 are preferred because of lower power consumption. Alternatively, it may be possible to use a single oscillator and interchange only the portion of the oscillator which determines the rate. This would still be viewed as two separate oscillator configurations, however.

The invention does not depend upon the specific details of the programmer console or a specific command or data format as the stored program can be modified to meet the needs of any reasonable format. The principles of the invention are not confined to multielectrode neural stimulators but are applicable to all implantable stimulators which operate by applying pulses of electricity to a stimulation electrode. While discrete components are used in the preferred embodiment for the parameter latches and pulse generation functions, this is not meant to exclude the possibility of implementing these functions in software executed by the same microprocessor that is used for programming or by a second microprocessor dedicated to the pulse generation function. Certain aspects of the system are not limited to stored program data processing systems and are applicable in general to stimulator implants. For example, the alternating polarity mode can be implemented entirely in hardware as can the dual clock energy conserving pulse generation system.

As various changes can be made in the above construction without departing from the scope of the invention, it should be understood that all matter contained in the above description or shown in the accompanying drawings shall be interpreted as illustrative and not in a limiting sense.

What is claimed is:

1. An implantable tissue stimulator, comprising
   at least one stimulation electrode,
   a slow clock,
   a fast clock,
   first and second presettable down counting means each producing a timed-output indicative of counting down to zero from a preset number, and each having a preset input and a clock input, said first and second counting clock inputs being connected to said slow clock and said fast clock respectively,
   means for enabling said fast clock in response to said timed-out output of said first counting means,
   logic means for beginning an output pulse in response to said timed-out output of said first counting means and ending said output pulse in response to the timed-out output of said second counting means,
   means for applying a stimulation output pulse corresonding to said output pulse from said logic means to said electrode,
   said means for enabling said fast clock including a fast clock enabler multiplexer having an output, and
   a clock selector multiplexer having a first input connected to the output of said fast clock enabler multiplexer and having a second input connected to said slow clock, said clock selector multiplexer applying selectively either the fast clock or slow clock to a clock input of a microprocessor.

2. The stimulator of claim 1, wherein said first and second counting means each include a respective preset enable input, the preset enable input of said first counting means being responsive to said timed-out output of said first counting means for recycling said first counting means and the preset enable input of said second counting means being responsive to the output of said logic means, and means for disabling said fast clock following said logic means output pulse.

3. The stimulator of claim 2, further comprising means responsive to an externally generated signal for disabling said slow clock.

4. The stimulator of claim 3, wherein said means for disabling said slow clock includes logic means for causing said slow clock to be disabled in response to said signal only when said fast clock is also disabled.

5. The stimulator of claim 1, wherein said slow and said fast clocks are separate oscillator circuits.

6. An implantable stimulator, comprising
   at least one stimulation electrode,
   a first clock,
   storage means containing a stored program,
   programmed microcomputer means having a clock input connected to said first clock for fetching and executing instructions in accordance with the stored program,
   interval timing means external to said microcomputer means, including a second clock, for disabling said first clock for predetermined variable time periods,
   means under the control of said microcomputer means for applying an output electrical stimulation pulse via said electrode, and
   multiplexer means responsive to said interval timing means for disconnecting said first clock from the clock input of said microcomputer means and for connecting said second clock to the clock input of said microcomputer means.

7. The stimulator of claim 6, wherein said interval timing means includes
   register means for storing a number indicative of a selected time interval,
   counter means having a clock input connected to said second clock for producing an output signal upon counting a number of second clock pulses corresponding to the number in said register means, and
   means responsive to said counter means output signal for re-enabling said first clock.

8. The stimulator of claim 7, wherein said microcomputer means has means for altering the number in said register.

* * * * *